US008980242B2

(12) United States Patent
Vetter et al.

(10) Patent No.: US 8,980,242 B2
(45) Date of Patent: Mar. 17, 2015

(54) ALIPHATIC PRODRUG LINKER

(75) Inventors: Dirk Vetter, Heidelberg (DE); Harald Rau, Heidelberg (DE); Thomas Wegge, Heidelberg (DE); Ulrich Hersel, Heidelberg (DE)

(73) Assignee: Ascendis Pharma GmbH, Hellerup (DK)

( * ) Notice: Subject to any disclaimer, the term of this patent is extended or adjusted under 35 U.S.C. 154(b) by 1791 days.

(21) Appl. No.: 11/993,645

(22) PCT Filed: Jun. 21, 2006

(86) PCT No.: PCT/EP2006/063418
§ 371 (c)(1),
(2), (4) Date: Jun. 21, 2010

(87) PCT Pub. No.: WO2006/136586
PCT Pub. Date: Dec. 28, 2006

(65) Prior Publication Data
US 2010/0291021 A1 Nov. 18, 2010

(30) Foreign Application Priority Data
Jun. 22, 2005 (GB) .................................. 0512705.5

(51) Int. Cl.
A61K 31/74 (2006.01)
A61K 47/48 (2006.01)
(52) U.S. Cl.
CPC ................................ A61K 47/48215 (2013.01)
USPC ....................................................... 424/78.27
(58) Field of Classification Search
None
See application file for complete search history.

(56) References Cited

U.S. PATENT DOCUMENTS

2004/0053976 A1   3/2004  Martinez et al.

FOREIGN PATENT DOCUMENTS

| WO | WO-9930727 A1 | 6/1999 |
| WO | WO-02083180 A1 | 10/2002 |
| WO | WO-02089789 A | 11/2002 |
| WO | WO-03070173 A1 | 8/2003 |
| WO | WO-2004014424 A1 | 2/2004 |
| WO | WO-2004019993 A1 | 3/2004 |
| WO | WO-2004043493 A1 | 5/2004 |
| WO | WO-2004085386 A1 | 10/2004 |
| WO | WO 2004108070 A2 * | 12/2004 |
| WO | WO-2004108070 A2 | 12/2004 |
| WO | WO-2006-066020 A2 | 6/2006 |
| WO | WO-2006065867 A2 | 6/2006 |

OTHER PUBLICATIONS

Na, D.H., et al., Monitoring of peptide acylation inside degrading PLGA microspheres by capillary electrophoresis . . . , J. Contr. Rel., 2003, 92, 291-299.
Duncan, R., The Dawning Era of Polymer Therapeutics, Nature Rev. Drug Disc., 2003, 2, 347-360.
Matsumura, Y. and Maeda, H., A New Concept for Macromolecular Therapeutics in Cancer Chemotherapy . . . , Cancer Research, Dec. 1986, 46, 6387-6392.
Caliceti, P., and Veronese, F., Adv. Drug Deliv. Rev., 2003, 55, 1261-1277.
Testa, B., Hydrolysis in Drug and Prodrug Metabolism, Wiley-VCH, 2003, 4-5.
Peleg-Shulman, T. et al., Reversible PEGylation: A Novel Technology To Release Native Interferon a2 over a Prolonged Time Period, J. Med. Chem., 2004, 47, 4897-4904.
Luo, Y., et al., A Hyaluronic Acid-Taxol Antitumor Bioconjugate Targeted to Cancer Cells, Biomacromolecules 2000, 1, 208-218.
Greenwald, R.B., et al., Drug Delivery Systems Employing 1, 4- or 1,6-Elimination: Poly(ethylene glycol) . . . , J. Med. Chem., 1999, 42, 3657-3667.
Cheng, J., et al., Synthesis of Linear, Beta-Cyclodextrin-Based Polymers and Their Camptothecin Conjugates, Biconjugate Chem., 2003, 14, 1007-1017.
Testa, B., et al., Hydrolysis in Drug and Prodrug Metabolism, Wiley-VCH, 2003, Chapter 8.
Bhatt, R., et al., Synthesis and in Vivo Antitumor Activity of Poly(L-glutamic acid) Conjugates of 20(S)-Camptothecin, J. Med. Chem., 2003, 46, 190-193.
Cavallaro, G., et al., Polymeric Prodrug for Release of an Antitumoral Agent by Specific Enzymes, Bioconjugate Chem., 2001, 12, 143-151.
Duncan, R., et al., Polymer-drug conjugates, PDEPT and PELT: basic principles for design and transfer from the laboratory to clinic, J. Contr. Release, 2001, 74, 135-146.
Satchi-Fainaro, R., et al., PDEPT: Polymer-Directed Enzyme Prodrug Therapy.2. HPMA Copolymer-beta-lactamase and HPMA . . . , Bioconjugate Chem., 2003, 14, 797-804.
Wiwattanapatapee, R., et al., Dendrimers conjugates for colonic delivery of 5-aminosalicylic acid, J. Controlled Release, 2003, 88, 1-9.
Greenwald, R., et al., Drug Delivery Systems Based on Trimethyl Lock Lactonization: Poly(ethylene glycol) Prodrugs of Amin-Containing . . . , J. Med. Chem., 2000, 43, 475-487.
Antczak, C. et al., A New Acivicin Prodrug Designed for Tumor-Targeted Delivery, Bioorg. Med. Chem. 9, 2001, 2843-2848.
Shabat, D., et al., Chemical Adaptor Systems, Chem. Eur. J., 2004, 10, 2626-2634.
Lee, M-R., et al., Targeted Enzyme-Responsive Drug Carriers: Studies on the Delivery of a Combination of Drugs, Angew. Chem., 2004, 116, 1707-1710.
Garman, A.J., Kalindjan, S.B., The preparation and properties of novel reversible polymer-protein conjugates, FEBS Letters, Nov. 1987, 223, 2, 361-365.
Greenwald, R., et al., A New Aliphatic Amino Prodrug System for the Delivery of Small Molecules and Proteins Utilizing Novel PEG Derivatives, J. Med. Chem., 2004, 47, 726-734.
Suggs, J.W., Pires, R.M., Facile Hydrolysis and Formation of Amide Bonds by N-Hydroxyethylation of a-Amino Acids, Tetrahedron Letters, Mar. 1997, 38, 13, 2227-2230.

* cited by examiner

*Primary Examiner* — Susan Tran
(74) *Attorney, Agent, or Firm* — Frommer Lawrence & Haug LLP

(57) ABSTRACT

A polymeric prodrug is described which comprises at least one polymer attached via at least one permanent bond to a bicine linker. The bicine linker is attached via a temporary linkage to an amine containing biologically active moiety. The amine containing biologically active moiety—such as a drug—can be released by cleaving the temporary linkage.

50 Claims, 10 Drawing Sheets

ALIPHATIC PRODRUG LINKER

FIELD

The present invention is directed to polymeric prodrugs having temporary linkages to amino groups of biologically active entities such as peptides, proteins, natural products or synthetic chemical compounds.

BACKGROUND

Typically, polymers in drug delivery are either used in a non-covalent fashion, with the drug physicochemically formulated into a solvent-polymer mixture, or by permanent covalent attachment of a polymer reagent to one of the drug's functional groups.

Non-covalent drug encapsulation has been applied to depot formulations for long-acting release profiles. Typically, the drug is mixed with polymer material and processed in such fashion, that the drug becomes distributed throughout the bulk polymer material. Such polymer-drug aggregates may be shaped as microparticles which are administered as an injectable suspension or the polymer-drug aggregates are formulated as gels which are administered in a single bolus injection. Drug release occurs when the polymer swells or degradation of the polymer allows diffusion of the drug to the exterior of the bulk polymer. Such degradation processes may be autohydrolytic or enzyme-catalyzed. An example for a marketed drug based on bolus administration of a drug-polymer gel is Lupron Depot. An example for a marketed drug based on suspended microparticles is Nutropin Depot.

A disadvantage of the non-covalent approach is that in order to prevent uncontrolled, burst-type release of the drug, encapsulation of the drug has to be highly efficient by creating a sterically highly crowded environment. Restraining the diffusion of an unbound, water soluble drug molecule requires strong van der Waals contacts, frequently mediated through hydrophobic moieties. Many conformationally sensitive drugs, such as proteins or peptides, are rendered dysfunctional during the encapsulation process and/or during subsequent storage of the encapsulated drug. In addition, such amino-containing drugs readily undergo side reactions with polymer degradation products (see, for example, D. H. Lee et al., J. Contr. Rel., 2003, 92, 291-299). Furthermore, dependence of the release mechanism of the drug upon biodegradation may cause interpatient variability.

Alternatively, the drugs may be conjugated to the polymers through permanent covalent bonds. This approach is applied to various classes of molecules, from so-called small molecules, through natural products up to larger proteins.

Many small molecule medicinal agents, like alkaloids and anti-tumor agents, show low solubility in aqueous fluids. One way to solubilize these small molecule compounds is to conjugate the small molecule compounds to hydrophilic (water-soluble) polymers. A variety of water-soluble polymers, such as human serum albumin, dextran, lectins, poly(ethylene glycol) (PEG), poly(styrene-co-maleic anhydride), poly(N-hydroxypropylmethacrylamide), poly(divinyl ether-co-maleic anhydride), hyaluronic acid have been described for this purpose (R. Duncan, Nature Rev. Drug Disc., 2003, 2, 347-360).

A major challenge in cancer therapy is to selectively target cytotoxic agents to tumor cells. A promising method to accumulate small molecule anticancer agents in tumor tissue and decrease undesirable side effects of these agents is the attachment of the cytotoxin to a macromolecular carrier. The passive targeting of polymeric drug conjugates to tumors is based on the so-called enhanced permeability and retention effect (EPR) as described by Matsumura, Y. and Maeda, H., in Cancer Res., 1986, vol 6, pp 6387-6392. As a result, several polymer-drug conjugates have entered clinical trial as anticancer agents.

Covalent modification of biological molecules with poly (ethylene glycol) has been extensively studied since the late 1970s. So-called PEGylated proteins have shown improved therapeutic efficacy by increasing solubility, reducing immunogenicity, and increasing circulation half-live in vivo due to reduced renal clearance and proteolysis by enzymes (see, for example, Caliceti P., Veronese F. M., Adv. Drug Deliv. Rev. 2003, 55, 1261-1277).

However, many biological molecules such as INFalfa2, saquinavir or somatostatin are inactive or show decreased biological activity when the polymer is covalently conjugated to the drug (T. Peleg-Shulman et al., J. Med. Chem., 2004, 47, 4897-4904).

In order to avoid shortcomings imposed by either the non-covalent polymer mixtures or the permanent covalent attachment, it may be preferable to employ a prodrug approach for chemical conjugation of the drug to the polymer carrier. In such polymeric prodrugs, the biologically active moieties (drugs, therapeutic, biological molecule, etc.) are typically linked to the polymeric carrier moiety by a temporary bond formed between the carrier moiety and a hydroxy, amino or carboxy group of the drug molecule.

Prodrugs are therapeutic agents that are almost inactive per se but are predictably transformed into active metabolites (see B. Testa, J. M: Mayer in Hydrolysis in Drug and Prodrug Metabolism, Wiley-VCH, 2003, page 4). The carrier prodrug approach may be applied in such a fashion that the drug is released in vivo from the polymer in order to regain its biological activity. The reduced biological activity of the prodrug as compared to the released drug is of advantage if a slow or controlled release of the drug is desired. In this case, a relatively large amount of prodrug may be administered without concomitant side effects and the risk of overdosing. Release of the drug occurs over time, thereby reducing the necessity of repeated and frequent administration of the drug.

Prodrug activation may occur by enzymatic or non-enzymatic cleavage of the temporary bond between the carrier and the drug molecule, or a sequential combination of both, i.e. an enzymatic step followed by a non-enzymatic rearrangement, as shown in FIG. 1. In an enzyme-free in-vitro environment such as an aqueous buffer solution, a temporary bond such as an ester or amide may undergo hydrolysis, but the corresponding rate of hydrolysis may be much too slow and not therapeutically useful. In an in-vivo environment, esterases or amidases are typically present and the esterases and amidases may cause significant catalytic acceleration of the kinetics of hydrolysis from twofold up to several orders of magnitude (see, for example, R. B. Greenwald et al. J. Med. Chem. 1999, 42 (18), 3857-3867).

Definitions Based on IUPAC
(as given under http://www.chem.qmul.ac.uk/iupac/med-chem/ (accessed on 8 Mar. 2004)

Prodrug

A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

Carrier-Linked Prodrug (Carrier Prodrug)

A carrier-linked prodrug is a prodrug that contains a temporary linkage of a given active substance with a transient carrier group that produces improved physicochemical or pharmacokinetic properties and that can be easily removed in vivo, usually by a hydrolytic cleavage. This is shown graphically in FIG. 1.

Cascade Prodrug

A cascade prodrug is a carrier prodrug for which the cleavage of the carrier group becomes effective only after unmasking an activating group.

Polymeric Cascade Prodrug

A polymeric cascade prodrug is a carrier prodrug that contains a temporary linkage of a given active substance with a transient polymeric carrier group for which the cleavage of the carrier becomes effective only after unmasking an activating group.

Bioprecursor Prodrug

A bioprecursor prodrug is a prodrug that does not imply the linkage to a carrier group, but results from a molecular modification of the active principle itself. This modification generates a new compound, able to be transformed metabolically or chemically, the resulting compound being the active principle.

Biotransformation

Biotransformation is the chemical conversion of substances by living organisms or enzyme preparations.

Further Definitions:

Linker

Cleavage-controlling chemical structures or groups present in carrier prodrugs that are provided by neither the carrier entity nor by the drug.

Prodrugs fall in two classes, bioprecursors and carrier-linked prodrugs. Bioprecursors do not contain a carrier group and are activated by the metabolic creation of a functional group. In carrier-linked prodrugs the active substance is linked to a carrier moiety by a temporary linkage. The carrier may be biologically inert (for instance PEG) or may have targeting properties (for instance antibodies). This invention is concerned with polymeric carrier-linked or macromolecular prodrugs, where the carrier itself is a macromolecule such as a carrier protein or polysaccharide or polyethylene glycol.

Cleavage of a carrier prodrug generates a molecular entity (drug) of increased bioactivity and at least one side product, the carrier. After cleavage, the bioactive entity will reveal at least one previously conjugated and thereby protected functional group, and the presence of this group typically contributes to the drug's bioactivity.

In order to implement a prodrug strategy, at least one selected functional group in the drug molecule is employed for attachment of the carrier polymer. Preferred functional groups are hydroxyl or amino groups. Consequently, both the attachment chemistry and hydrolysis conditions depend on the type of functional group employed. In a simple one-step cleavage mechanism, the prodrug's temporary linkage is often characterized by an intrinsic lability or enzyme dependence. The susceptibility of this linkage to hydrolysis in an aqueous environment with or without enzyme catalysis controls the cleavage kinetics between polymeric carrier and drug.

Numerous macromolecular prodrugs are described in the literature where the temporary linkage is a labile ester bond. In theses cases, the functional group provided by the bioactive entity is either a hydroxyl group or a carboxylic acid (e.g. Y. Luo, M R Ziebell, G D Prestwich, "A Hyaluronic Acid—Taxol Antitumor Bioconjugate Targeted to Cancer Cells", Biomacromolecules 2000, 1, 208-218, J Cheng et al, Synthesis of Linear, beta-Cyclodextrin Based Polymers and Their Camptothecin Conjugates, Bioconjugate Chem. 2003, 14, 1007-1017, R. Bhatt et al, Synthesis and in Vivo Antitumor Activity of Poly(L-glutamic acid) Conjugates of 20(S)-Campthothecin, J. Med. Chem. 2003, 46, 190-193; R. B. Greenwald, A. Pendri, C. D. Conover, H. Zhao, Y. H. Choe, A. Martinez, K. Shum, S. Guan, J. Med. Chem., 1999, 42, 3657-3667; B. Testa, J. M: Mayer in Hydrolysis in Drug and Prodrug Metabolism, Wiley-VCH, 2003, Chapter 8).

Especially for therapeutic biomacromolecules but also for certain small molecule drugs, it may be desirable to link the macromolecular carrier to amino groups of the bioactive entity (i.e. N-terminus or lysine amino groups of proteins). This will be the case if masking the drug's bioactivity requires conjugation of a certain amino group of the bioactive entity, for instance an amino group located in an active center or a region or epitope involved in receptor binding. Also, during preparation of the prodrug, the amino groups may be more chemoselectively addressed and serve as a better handle for conjugating the carrier and the drug because of their greater nucleophilicity as compared to hydroxylic or phenolic groups. This is particularly true for proteins which may contain a great variety of different reactive functionalities, where non-selective conjugation reactions lead to undesired product mixtures which require extensive characterization or purification and may decrease reaction yield and therapeutic efficiency of the product.

Amide bonds as well as aliphatic carbamates are usually much more stable against hydrolysis than ester bonds, and the rate of cleavage of the amide bond would be too slow for therapeutic utility in a carrier-linked prodrug. Therefore it is advantageous to add structural chemical components such as neighbouring groups in order to exert control over the cleavability of the prodrug amide bond. Such additional cleavage-controlling chemical structures that are not provided neither by the carrier entity nor by the drug are termed "linkers". Prodrug linkers can have a strong effect on the rate of hydrolysis of a given temporary bond. Variation of the chemical nature of these linkers allows the engineering of the properties of the linker to a great extent.

Several examples have been published of the prodrug activation of amine-containing biologically active moieties by specific enzymes for targeted release. A prerequisite for enzymatic dependence is that the structure of the linker displays a structural motif that is recognized as a substrate by a corresponding endogenous enzyme (such as shown in FIG. 2). In these cases, the cleavage of the temporary bond occurs in a one-step process which is catalyzed by the enzyme. G. Cavallaro et al., Bioconjugate Chem. 2001, 12, 143-151 describe the enzymatic release of an antitumoral agent by the protease plasmin. Cytarabin is coupled via the tripeptide sequence D-Val-Leu-Lys to the polymer alpha, beta-poly(N-hydroxyethyl)-DL-aspartamide (PHEA). Enzymatic release of cytarabin is effected by the protease plasmin which concentration is relatively high in various kinds of tumor mass.

Enzyme-catalyzed acceleration of prodrug cleavage is a desirable feature for organ or cellular targeting applications. Targeted release of the bioactive entity is effected, if an enzyme, that selectively cleaves the linkage, is specifically present in the organ or cell-type chosen for treatment.

A typical property of an enzyme-dependent temporary linkage is its stability with respect to hydrolysis. The enzyme-dependent temporary linkage itself will not undergo autohydrolysis at a rate that would release the drug to such an extent that the therapeutic effect of the drug could be induced in a normal dosing regime. It is only in the presence of the enzyme, that the attack of the enzyme on the enzyme-dependent temporary linkage causes a significant acceleration of cleavage of the enzyme-dependent temporary linkage and concomitantly an enhancement of the concentration of the free drug.

Further examples for antitumoral polymeric prodrugs activated by specific enzymes like beta lactamase (R. Satchi-Fainaro et al., Bioconjugate Chem. 2003, 14, 797-804) and cysteine proteases like cathepsin B (R. Duncan et al. J. Contr. Release 2001, 74, 135-146) have been described. Wiwattanapatapee et al. (2003) outline a dendrimer prodrug for colonic delivery of 5-aminosalicylic acid. The drug molecule is conjugated by an azo bond to "generation 3" PAMAM dendrimer. 5-aminosalicylic acid is released in the colon by a bacterial enzyme called azo reductase (W. R. Wiwattanapatapee, L. Lomlim, K. Saramunee, J. Controlled Release, 2003, 88: 1-9).

A major drawback of predominantly enzymatic cleavage is interpatient variability. Enzyme levels may differ significantly between individuals resulting in biological variation of prodrug activation by the enzymatic cleavage. The enzyme levels may also vary depending on the site of administration. For instance it is known that in the case of subcutaneous injection, certain areas of the body yield more predictable therapeutic effects than others. To reduce this unpredictable effect, non-enzymatic cleavage or intramolecular catalysis is of particular interest (see, for example, B. Testa, J. M: Mayer in Hydrolysis in Drug and Prodrug Metabolism, Wiley-VCH, 2003, page 5).

Furthermore, it is difficult to establish an in vivo-in vitro correlation of the pharmacokinetic properties for such enzyme-dependent carrier-linked prodrugs. In the absence of a reliable in vivo-in vitro correlation optimization of a release profile becomes a cumbersome task.

Other polymeric prodrugs employing temporary linkages to amino groups present in the drug molecule are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino-group of the drug molecule through a second temporary linkage, for instance a carbamate. The stability, or susceptibility to hydrolysis of the second temporary linkage (e.g. carbamate) is dependent on the presence or absence of the masking group. In the presence of the masking group, the second temporary linkage is highly stable and unlikely to release the drug with therapeutically useful kinetics. In the absence of the masking group, this linkage becomes highly labile, causing rapid cleavage and drug release.

The cleavage of the first temporary linkage is the rate-limiting step in the cascade mechanism. This first step may induce a molecular rearrangement of the activating group such as a 1,6-elimination. The rearrangement renders the second temporary linkage so much more labile that its cleavage is induced. Ideally, the cleavage rate of the first temporary linkage is identical to the desired release rate for the drug molecule in a given therapeutic scenario. Furthermore, it is desirable that the cleavage of the second temporary linkage is substantially instantaneous after its lability has been induced by cleavage of the first temporary bond (see FIG. 3).

Examples of such polymeric prodrugs based on 1,6 elimination have been described by R. B. Greenwald et al. J. Med. Chem., 1999, 42, 3657-3667 & PCT Patent Application WO-A-99/30727, F. M. H. DeGroot et al. (WO02083180 and WO04043493A1), and D. Shabat et al. (WO04019993A1).

Examples of polymeric amino-containing prodrugs based on trimethyl lock lactonization were described by R. B. Greenwald et al. J. Med. Chem. 2000, 43(3), 457-487; PCT Patent Application No. WO-A-02/089789). In this prodrug system, substituted o-hydroxyphenyl-dimethylpropionic acid is linked to PEG by an ester, carbonate, or carbamate group as a first temporary linkage and to amino groups of drug molecules by means of an amide bond as second temporary linkage. The rate-determining step in drug release is the enzymatic cleavage of the first linkage. This step is followed by fast amide cleavage by lactonization, liberating an aromatic lactone side product.

The disadvantage in the abovementioned prodrug systems described by Greenwald, DeGroot and Shabat is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

A different group of cascade prodrugs with aromatic activating groups based on 1,6 elimination structurally separates the masking group and the carrier. This may be achieved by employing a permanent bond between polymer carrier and activating group. This stable bond does not participate in the cascade cleavage mechanism. If the carrier is not serving as a masking group and the activating group is coupled to the carrier by means of a stable bond, release of potentially toxic side products such as the activating group is avoided. The stable attachment of the activating group and the polymer also suppresses the release of drug-linker intermediates with undefined pharmacology.

Antczak et al. (Bioorg Med Chem 9 (2001) 2843-48) describe a reagent which forms the basis for a macromolecular cascade prodrug system for amine-containing drug molecules. In this approach an antibody serves as the carrier, a stable bond connects the antibody to an activating group, carrying an enzymatically cleavable masking group. Upon enzymatic removal of the ester-linked masking group, a second temporary bond cleaves and releases the drug compound, as shown in FIG. 4.

D. Shabat et al. (Chem. Eur. J. 2004, 10, 2626-2634) describe a polymeric prodrug system based on a mandelic acid activating group. In this system the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released. The activating group is still connected to the polyacrylamide polymer after drug release.

M.-R. Lee et al. describe (Angew. Chem. 2004, 116, 1707-1710) a similar prodrug system based on mandelic acid activating group and an enzymatically cleavable ester-linked masking group.

Nevertheless in these linkers a 1,6 elimination step still generates a highly reactive aromatic intermediate. Even if the aromatic moiety remains permanently attached to the polymeric carrier, side reactions with potentially toxic or immunogenic effects may be caused.

For these reasons, there is a need to provide novel linker technologies for forming polymeric prodrugs of amine containing active agents using aliphatic prodrug linkers that are not enzyme-dependent and do not generate reactive aromatic intermediates during cleavage.

A. J. Garman et al. (A. J. Garman, S. B. Kalindjan, FEBS Lett. 1987, 223 (2), 361-365 1987) use PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid linkage follows first order kinetics with a half-life of 6.1 h. A disadvantage of the maleamic acid linkage is the lack of stability of the conjugate at lower pH values. This limits the applicability of the maleamic acid linkage to active agents which are stable at basic (high) pH values, as purification of the active agent polymer conjugate has to be performed under basic (high pH) conditions to prevent premature prodrug cleavage.

More recently, R. B. Greenwald et al. (Greenwald et al. J. Med. Chem. 2004, 47, 726-734 and WO 2004/108070A2) described a PEG cascade prodrug system based on N,N-bis-(2-hydroxyethyl)glycine amide (bicine) linker. In the system described in the Greenwald et al paper and patent application two PEG carrier molecules are linked via temporary bonds to a bicine molecule coupled to an amino group of the drug molecule. The first two steps in prodrug activation is the enzymatic cleavage of the first temporary linkages connecting both PEG carrier molecules with the hydroxy groups of the bicine activating group. Different linkages between PEG and bicine are described resulting in different prodrug activation kinetics. The second step in prodrug activation is the cleavage of the second temporary linkage connecting the bicine activating group to the amino group of the drug molecule (FIG. 5). The main disadvantage of this system is the connection of the polymer to the bicine linker via temporary bonds and the slow hydrolysis rate of this second temporary bicine amide linkage ($t_{1/2} > 3$ h in phosphate buffer) which results in the release of a bicine-modified prodrug intermediate that may show different pharmacokinetic, immunogenic, toxicity and pharmacodynamic properties as compared to the parent native drug molecule.

DETAILED DESCRIPTION OF THE INVENTION

The present invention addresses the disadvantages described above. The invention provides for polymeric prodrugs characterized by connecting a polymer via a bicine linker to a primary or secondary amino group of an amine-containing drug molecule, whereby the polymer is linked to the bicine linker via a permanent linkage and the bond between the bicine linker and the amine-containing drug molecule is the temporary linkage. Bicine is used in this application as synonym for N,N-bis(2-hydroxyethyl)-glycyl or N,N-bis(2-hydroxyethyl)-glycine amide or N,N-bis(2-hydroxy)glycine. Due to the presence of a permanent bond between the carrier and the bicine linker the polymeric prodrugs according to the present invention ensure release of unmodified native drug molecules (FIG. 6).

The invention provides for polymeric prodrugs and corresponding polymeric linker reagents of Formula Ia, Ib, or Ic.

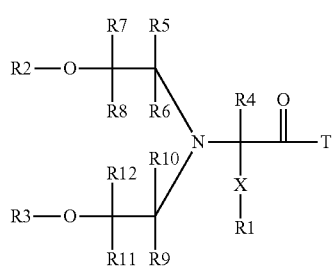

Ia

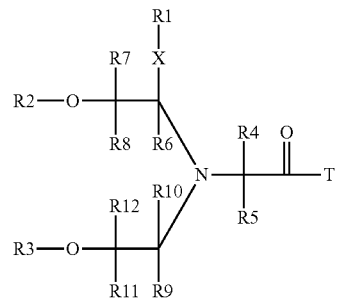

Ib

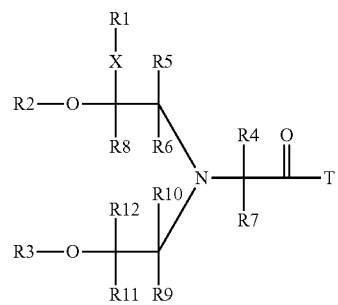

Ic wherein T, X, and R1 to R12 are defined below:

Native drug release from a polymeric prodrug according to the present invention by hydrolytic cleavage of the polymer substituted bicine residue is exemplified by a polymeric prodrug according to formula Ia where R2 to R12 are hydrogen.

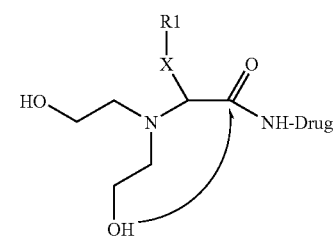

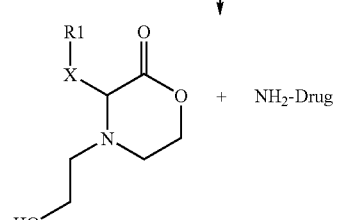

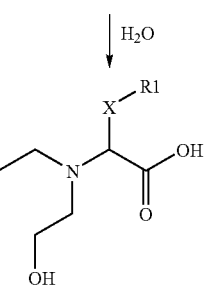

As described above, release of the native drug from the polymeric carrier may be mediated by an enzymatic or a non-enzymatic step, such as pH-dependent hydrolysis or intramolecular cyclization. In the preferred embodiment of the invention, cleavage is effected non-enzymatically. The half-life of the cleaveage kinetics in an aqueous buffer of pH 7.4 at 37° C. of the polymeric prodrug according to the present invention is preferably between 3 hours and 6 months, more preferably between 1 day and 3 months, and most preferably between 1 day and 2 months.

Definition of X, T, R1 to R12 in Formula Ia, Ib, or Ic

T is D or A

In the case where the inventive structure is a polymeric prodrug linker reagent, T is A, and A is a leaving group. Non-limiting examples of suitable leaving groups A include but are not limited to chloride, bromide, fluoride, nitrophenoxy, imidazolyl, N-hydroxysuccinimidyl, N-hydroxybenzotriazolyl, N-hydroxyazobenzotriazolyl, pentafluorphenoxy, N-hydroxysulfosuccinimidyl, or any other leaving group known by those skilled in the art.

In the case where the inventive structure is a polymeric prodrug, T is D, and D is a residue of an amine-containing biologically active material including but not limited to small molecule bioactive moieties or biopolymers like proteins, polypeptides and oligonucleotides (RNA, DNA), peptide nucleic acids (PNA).

Note that in this description reference is often made to prodrugs. A true prodrug is found when T is the residue of the amine-containing biologically active material or moiety. If T is a leaving group A, then the formula represents a polymeric prodrug linker reagent. For simplicity the polymeric Prodrug linker reagent will also be referred to prodrugs in this description. It will be understood from the context whether a true prodrug or a polymeric Prodrug linker reagent is meant.

Suitable organic small molecule bioactive moieties include, without limitation, moieties such as central nervous system-active agents, anti-infective, anti-neoplastic, antibacterial, anti-fungal, analgesic, contraceptive, anti-inflammatory, steroidal, vasodilating, vasoconstricting, and cardiovascular agents with at least one primary or secondary amino group. Non-exclusive examples of such compounds are daunorubicin, doxorubicin, idarubicin, mitoxantron, aminoglutethimide, amantadine, diaphenylsulfon, ethambutol, sulfadiazin, sulfamerazin, sulfamethoxazol, sulfalen, clinafloxacin, moxifloxacin, ciprofloxaxin, enoxacin, norfloxacin, neomycin B, sprectinomycin, kanamycin A, meropenem, dopamin, dobutamin, lisinopril, serotonin, carbutamid, acivicin, etc.

Suitable proteins and polypeptides having at least one free amino group include but are not limited to ACTH, adenosine deaminase, agalsidase, albumin, alfa-1 antitrypsin (AAT), alfa-1 proteinase inhibitor (API), alteplase, anistreplase, ancrod serine protease, antibodies (monoclonal or polyclonal, and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietin, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idumonidase, immune globulins, influenza vaccines, interleukins (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines, plant proteins such as lectins and ricins.

Also included herein is any synthetic polypeptide or any portion of a polypeptide with in vivo bioactivity. Furthermore, proteins prepared by recombinant DNA methodologies including mutant versions of aforementioned proteins, antibody fragments, single chain binding proteins, catalytic antibodies and fusion proteins are included.

Preferred proteins are antibodies, calcitonin, G-CSF, GM-CSF, erythropoietins, hemoglobins, interleuldns, insulins, interferons, SOD, somatropin, TNF, TNF-receptor-IgG Fc, and GLP-1.

X is a spacer moiety such as R13-Y1.

Y1 is O, S, NR6, succinimide, maleimide, unsaturated carbon-carbon bonds or any heteratom containing a free electron pair, or is not present.

R13 is selected from substituted or non-substituted linear, branched or cyclical alkyl or heteroalkyl, aryls, substituted aryls, substituted or non-substituted heteroaryls, etc.

R2 and R3 are selected independently from hydrogen, acyl groups including polymeric acyl groups, or protecting groups for hydroxyl groups such as trityl, methoxytrityl, dimethoxytrityl, and other protecting groups known to the person skilled in the art. Suitable protecting groups are described in T W Greene, P. G. M. Wuts, Protective groups in organic synthesis, 1999, John Wiley & Sons, $3^{rd}$ ed.

R4 to R12 are selected independently from hydrogen, X—R1, substituted or non-substituted linear, branched or cyclical alkyl or heteroalkyl, aryls, substituted aryls, substituted or non-substituted heteroaryls, cyano, hydroxyl, nitro, halogen, carboxy, carboxamide, etc.

R4 to R12 are preferably selected independently from hydrogen, substituted or non-substituted linear, branched or cyclical $C_1$ to $C_8$ alkyl or heteroalkyl.

R4 to R12 are most preferably hydrogen.

The term "heteroalkyl" in the context of the present invention denotes (linear, cyclical or branched) alkyl chains where the alkyl chains contain or are substituted with at any position one or more heteroatoms, selected independently from O, S, N, P, Si, Cl, F, Br, I, etc. or groups, selected independently from carboxamide, carboxylic ester, phosphonate ester, phosphate ester, double or triple bonds, carbamate, urea, thiourea, thiocarbamate, oxime, cyano, carboxyl, carbonyl, etc.

R1 is a polymer.

Non-limiting examples for suitable polymers are polyalkyloxy-based polymers like poly(propylene glycol) or polyethylene glycol), dextran, chitosan, hyaluronic acid and derivatives, alginate, xylan, mannan, carrageenan, agarose, cellulose, starch, hydroxyethyl starch (HES) and other carbohydrate-based polmers, poly(vinyl alcohols), poly(oxazolines), poly(anhydrides), poly(ortho esters), poly(carbonates), poly(urethanes), poly(acrylic acids), polyacrylamides) such as poly(hydroxypropylmethacrylamide) (HMPA), poly (acrylates), poly(methacrylates) like poly(hydroxyethylmethacrylate), poly(organophosphazenes), poly(siloxanes), poly(vinylpyrrolidone), poly(cyanoacrylates), poly(esters)

such as poly(lactic acid) or poly(glycolic acids), poly(iminocarbonates), poly(amino acids) such as poly(glutamic acid), collagen, gelatin, copolymers, grafted copolymers, cross-linked polymers, hydrogels, and block copolymers from the above listed polymers.

Hydrogels may be defined as three-dimensional, hydrophilic or amphiphilic polymeric networks imbibing large quantifies of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. (see: N. A. Peppas, P. Bures, W. Leobandung, H. Ichikawa, Hydrogels in pharmaceutical formulations, Eur. J. Pharm. Biopharm. 2000, 50, 27-46). The chains of the network are connected in such a fashion that pores exist and that a substantial fraction of these pores are of dimensions of between 1 and 1000 nm. By selecting certain polymerization conditions, the hydrogel may be obtained in the form of an amorphous gel or as beaded resin. Such soft beads may have a diameter of between 1 and 1000 micrometer.

Hydrogels may be synthesized from the polymers and copolymers listed above and physically cross-linked or chemically cross-linked by radical, anionic or cationic polymerization, by chemical reactions like condensation or addition reactions as described in W. E. Hennink and C. F. van Nostrum, Adv. Drug Del. Rev. 2002, 54, 13-36.

Further examples include branched and hyperbranched polymers. Examples for such polymers include dendrimers and other dense star polymers. (R. Esfand, D. A. Tomalia, Drug Discov Today, 2001, 6(8), 427-436; P. M. Heegaard, U. Boas, Chem. Soc. Rev. 2004 (33(1), 43-63; S. M. Grayson, J. M. Frechet, Chem. Rev. 2001, 101 (12), 3819-3868).

R1 can also be a biopolymer like a protein. Non-limiting examples of such polymers include albumin, antibodies, transferrin, fibrin, casein, and other plasma proteins.

Each R1 polymer can carry one or more biologically active substances linked to the polymer by conjugation with a second prodrug linker as described herein or any other linker known to the person skilled in the art. The polymers may have further substituents and may be functionalized for attachment to the spacer moiety X. Non-limiting examples of such functional groups comprise carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphoric acid and derivatives, haloacetyl, alkyl halides, acryloyl, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

Preferred functional groups for the R1 polymer include but are not limited to thiol, maleimide, amino, carboxylic acid and derivatives, carbonate and derivatives, carbamate and derivatives, aldehyde, and haloacetyl.

Especially preferred functional groups include thiol, maleimide, amino, carboxylic acid and derivatives, carbamate and derivatives, and carbonate and derivatives thereof.

Non-limiting examples for suitable bonds or groups formed between X and R1 include disulfide, S-succinimido, amide, amino, carboxylic ester, sulfonamide, carbamate, carbonate, ether, oxime, thioether, hydrazone, urea, thiourea, phosphate, phosphonate, etc.

Preferred bonds or groups formed between X and R1 comprise S-succinimido, amide, carbamate, and urea.

Preferably, the R1 polymers are well hydrated, degradable or excretable, nontoxic and non-immunogenic in mammals. Preferred R1 polymers include polyalkoxy-based polymers like polyethylene glycol and polyethylene glycol reagents as those described in Nektar Inc. 2003 catalog "Nektar Molecule Engineering—Polyethylene Glycol and Derivatives for Advanced PEGylation" and branched, hyperbranched, cross-linked polymers and hydrogels, and proteins like albumin General Synthesis Procedures of the Polymeric Prodrugs Synthesis of representative examples of polymeric prodrugs according to the present invention is described in the Examples section.

Prodrugs of the present invention can be prepared in various different fashions. FIG. 8 shows a first general route for the synthesis of the polymeric prodrugs of the present invention according to formula Ic.

In this first method, solid-phase immobilized intermediate (IV) is provided by displacing leaving group A of immobilized starting material (III) with starting material (II). Optionally, this substitution may take place in solution with soluble starting material (III). X in (III) may be protected with a suitable protecting group PG. Suitable protecting groups are described in T W Greene, P. G. M. Wuts, Protective groups in organic synthesis, 1999, John Wiley & Sons, $3^{rd}$ ed.

Intermediate (V) is cleaved from the solid phase and all protecting groups are cleaved with reagents like trifluoroacetic acid or DTT. Intermediate (V) is then reacted with polymer R1 to yield the polymeric prodrug (Ica).

Polymeric prodrugs according to formula Ib can be prepared by similar methods known to the person skilled in the art as described above for prodrugs according to formula Ic using for example starting material IIa.

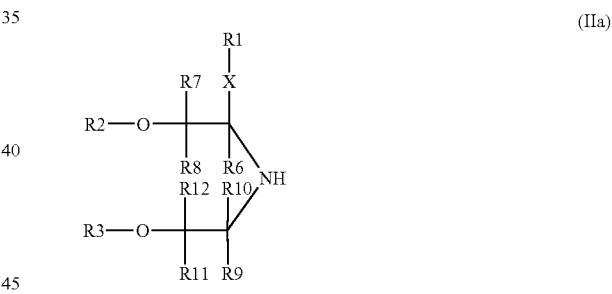

(IIa)

FIG. 9 shows a second general route for the synthesis of the polymeric prodrugs of the present invention according to formula Ia.

In this second method, solid-phase immobilized intermediate (VII) is provided from starting material (VI) by one or two nucleophilic substitution steps or one or two reductive alkylation steps. Optionally, this substitution or reductive alkylation steps may be carried out in solution with soluble starting material (VI). X in (III) may be protected with a suitable protecting group PG.

Intermediate (VIII) is cleaved from the solid phase and all protecting groups are cleaved with reagents like trifluoroacetic acid or DTT. Intermediate (VIII) is then reacted with polymer R1 to yield the polymeric prodrug (Iaa).

FIG. 10 shows a further general route for the synthesis of the polymeric prodrugs of the present invention according to formula Ia.

In this method, solid-phase immobilized intermediate (X) is provided from starting material (IX) by one or two nucleophilic substitution steps or one or two reductive alkylation steps. Optionally, this substitution or reductive alkylation steps may be carried out in solution with soluble starting material (IX). X in (X) may be protected with a suitable protecting group PG. Intermediate (XI) is cleaved from the solid phase with reagents like hexafluoro-isopropanol without cleavage of the protecting group.

In a first route, intermediate (XI) is activated with reagents such as carbodiimides and N-hydroxysucdnimide to yield (XII). Intermediate (XII) is reacted with an amine containing drug molecule to yield intermediate (XIII). After cleavage of the protecting group PG from intermediate (XIII) the compound is reacted with the polymer R1 to yield the polymeric prodrug Iaa.

In a second route, protecting group PG is cleaved from (XI) with reagents such as trifluoroacetic acid or DTT and the residue is reacted with polymer R1 to yield intermediate (XIV). Intermediate (XIV) is activated with reagents such as carbodiimides and N-hydroxysuccinimide to yield intermediate (XV), which is reacted with amine containing drug to form the polymeric prodrug Iaa.

In a third route, protecting group PG is cleaved from activated intermediate (XII) and the residue is reacted with polymer R1 to yield intermediate (XV), which is then reacted with amine containing drug to form the polymeric prodrug Iaa.

It is understood, that linker structures according to the outlined invention and carrying protecting groups or leaving groups as described and used in the synthesis of corresponding polymeric prodrugs are considered within the range of the invention.

Application of the Polymeric Prodrugs in Molecular Therapy

A key advantage of the present invention is the release of an unmodified biologically active moiety from the polymeric prodrug. In the prodrugs described by Greenwald et al. (Greenwald et al. J. Med. Chem. 2004, 47, 726-734) the biologically active moiety is released from the polymeric carrier as a bicine modified drug molecule with unpredictable pharmacokinetic, immunogenic, toxicity and pharmacodynamic properties. The release of the bicine modified drug molecule is impossible in the prodrugs according to the present invention due to the permanent linkage of the polymer carrier to the bicine linker.

For polymeric prodrugs it is desirable for the cleavage kinetics of the temporary linkage to proceed under conditions present in the blood of the human body (pH 7.4, 37° C.). Most importantly, cleavage of the temporary linkage should be based on hydrolysis and exhibit none or only very limited dependence upon chemical or biochemical or physicochemical entities present in the human blood such as enzymes, salts or binding proteins.

A further key advantage of the polymeric prodrugs of the present invention is their predominantly non-enzymatic cleavage: the half-life of the prodrug in vivo is at least 50% of the half-life of the prodrug in an enzyme-free buffer having pH 7.4. This predominantly non-enzymatic cleavage allows for better predictability and control of the release rates after administration to a living organism and reduces interpatient variability.

It was now surprisingly found that the rate of cleavage of the temporary linkage connecting the bicine linker with the amino group of the drug molecule can be controlled by neighbouring group effects mediated by different substitutions or polymer attachments of the bicine linker. The release rates are governed by a substantially non-enzymatic chemical reaction which is in turn dependent on the molecular structure of the linker. Systematic or random modifications of the chemical structure, for instance by changing the site of polymer attachment at the bicine linker allows for the generation of prodrug linkers with differing release rates. It is therefore possible to create a variety of prodrug linkers and select those fast or slow cleaving prodrug linkers according to the demands posed by a given medicinal or therapeutic application.

Enzyme-independent release control enables depot formulations without the need for encapsulation. Until now, many biocompatible materials like hydrogels with large pore sizes could not be used for depot formulations due to their lack of encapsulation properties. From such well-hydrated and mechanically soft biocompatible materials, the biologically active moiety would be released too fast for most therapeutic applications. In combination with the prodrug linkers described in this invention, the carrier material may be optimized for its biocompatibility properties as the release is solely governed by the linker cleavage kinetics and does not require chemical or enzymatic degradation of the polymer carrier itself.

EXAMPLES

Materials

Figure 1:
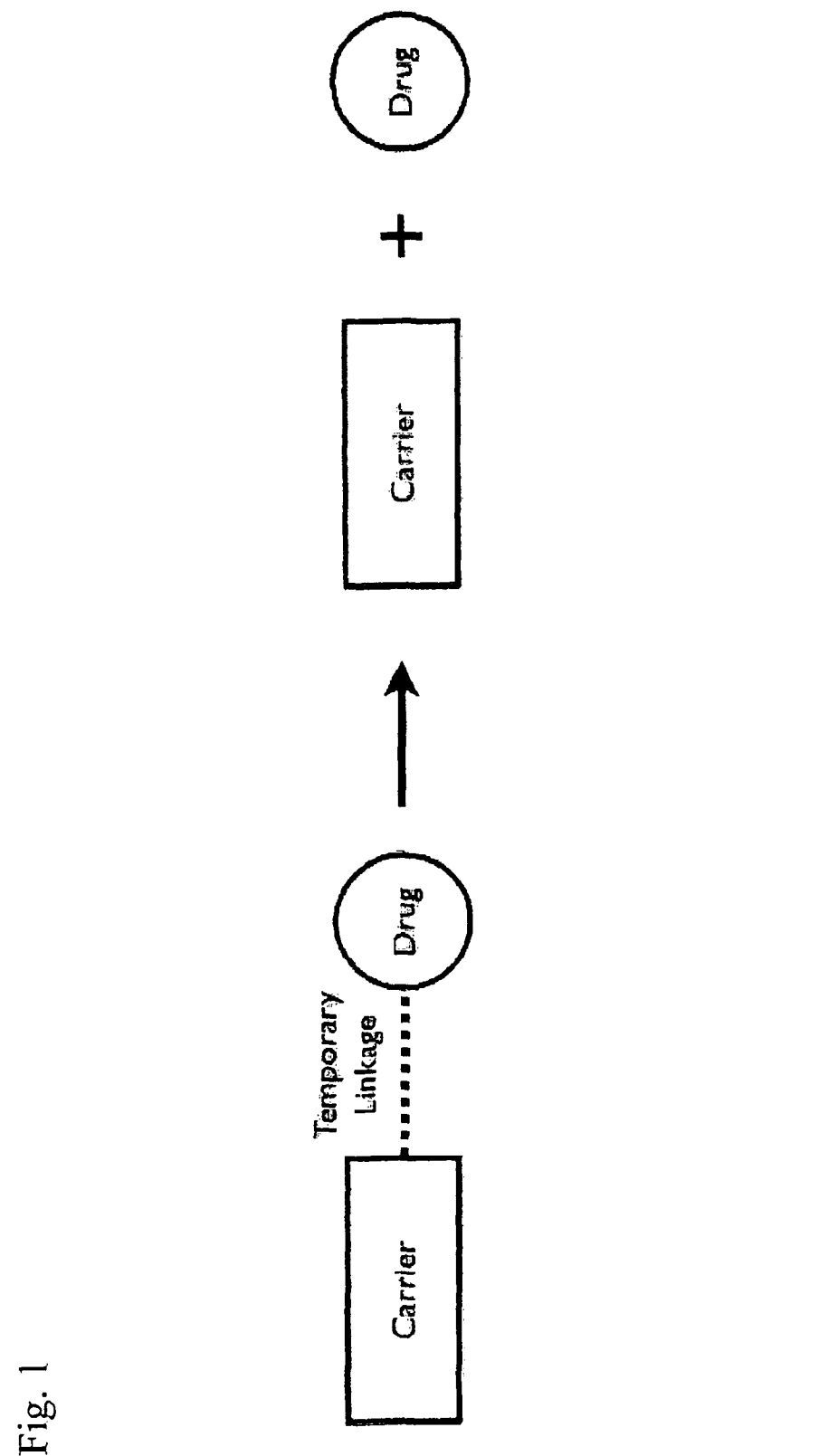
FIG. 1 shows a carrier-linked prodrug.
Figure 2:
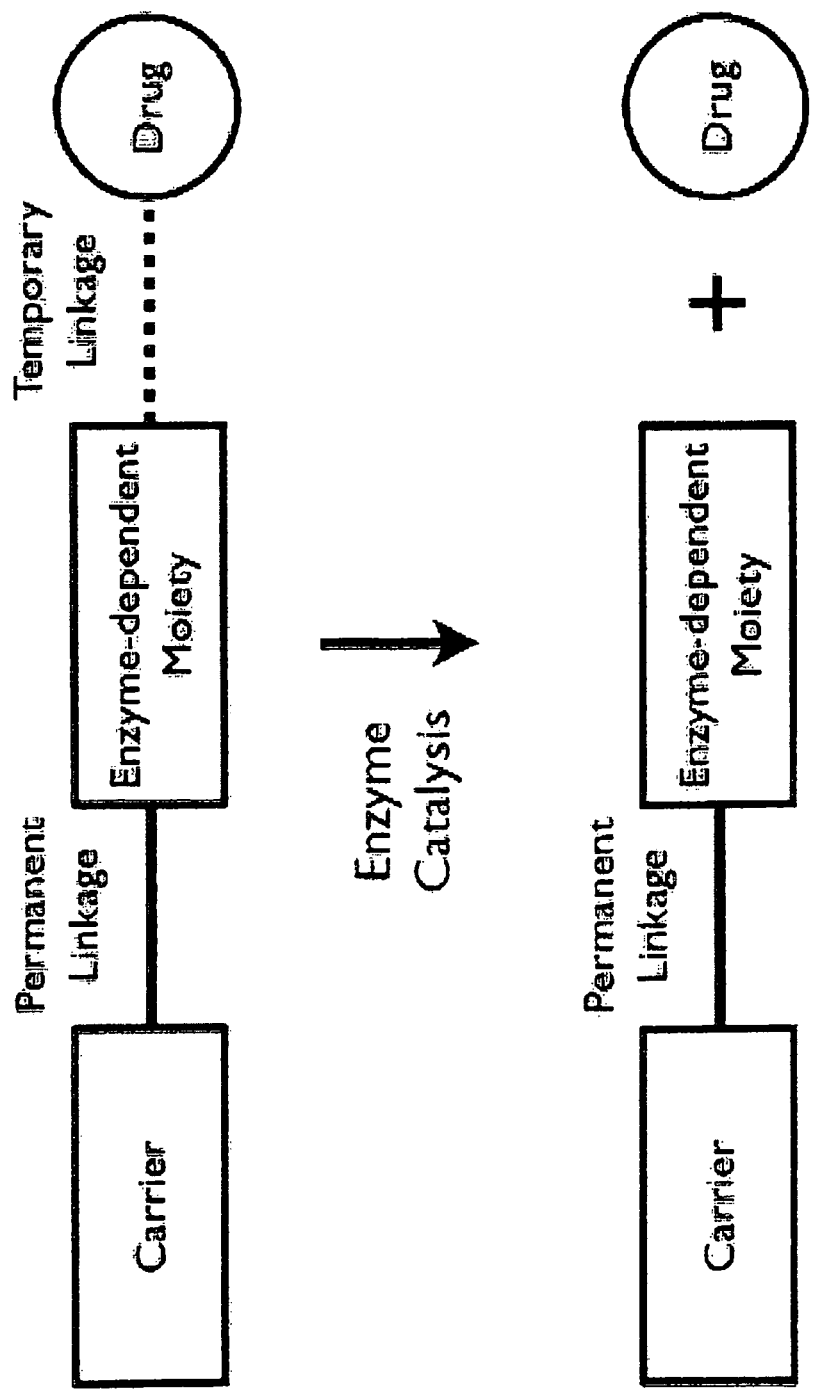
FIG. 2 shows an enzyme-dependent carrier-linked prodrug.
Figure 3:
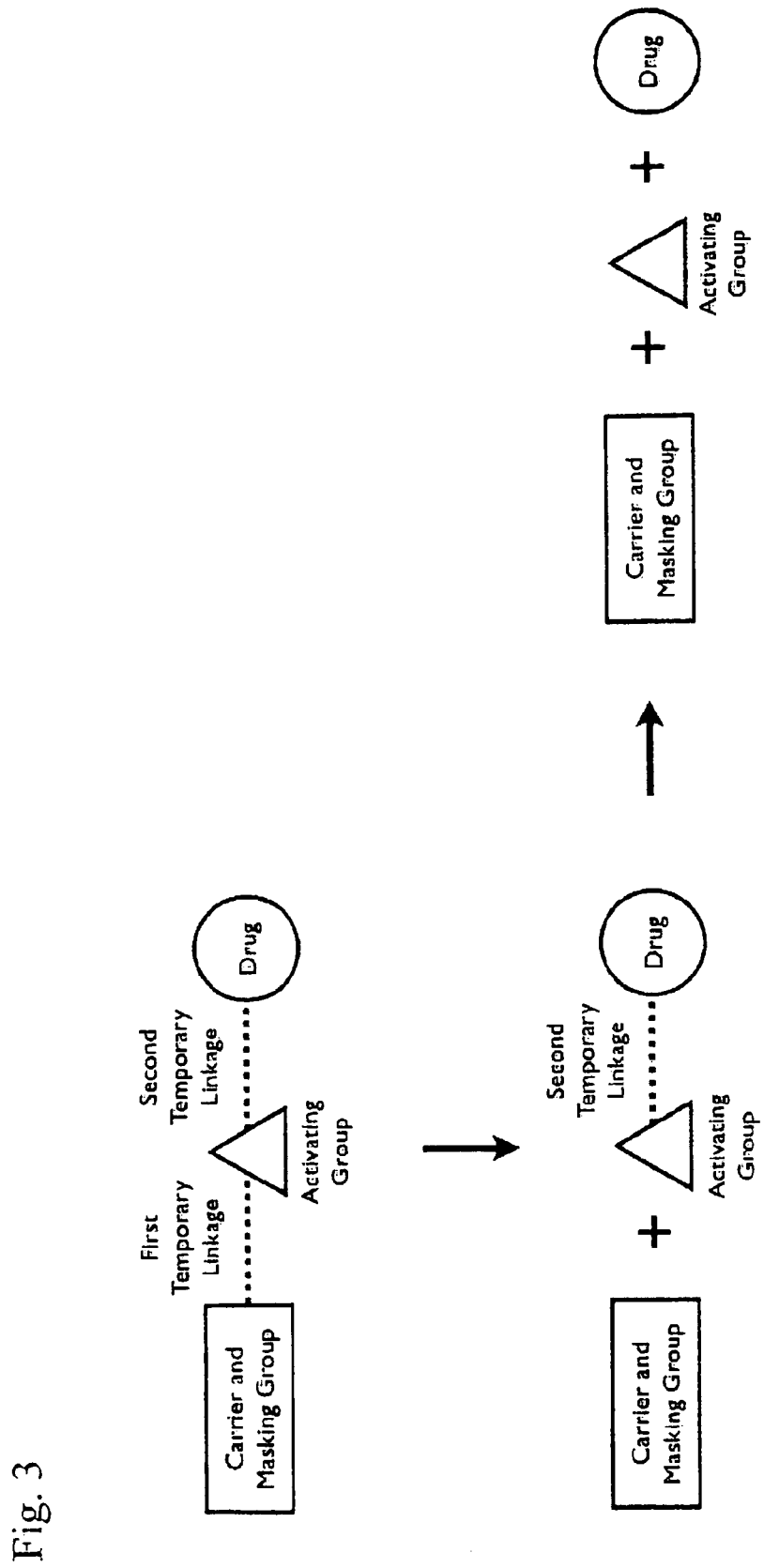
FIG. 3 shows a cascade prodrug where the masking group is part of the carrier.
Figure 4:
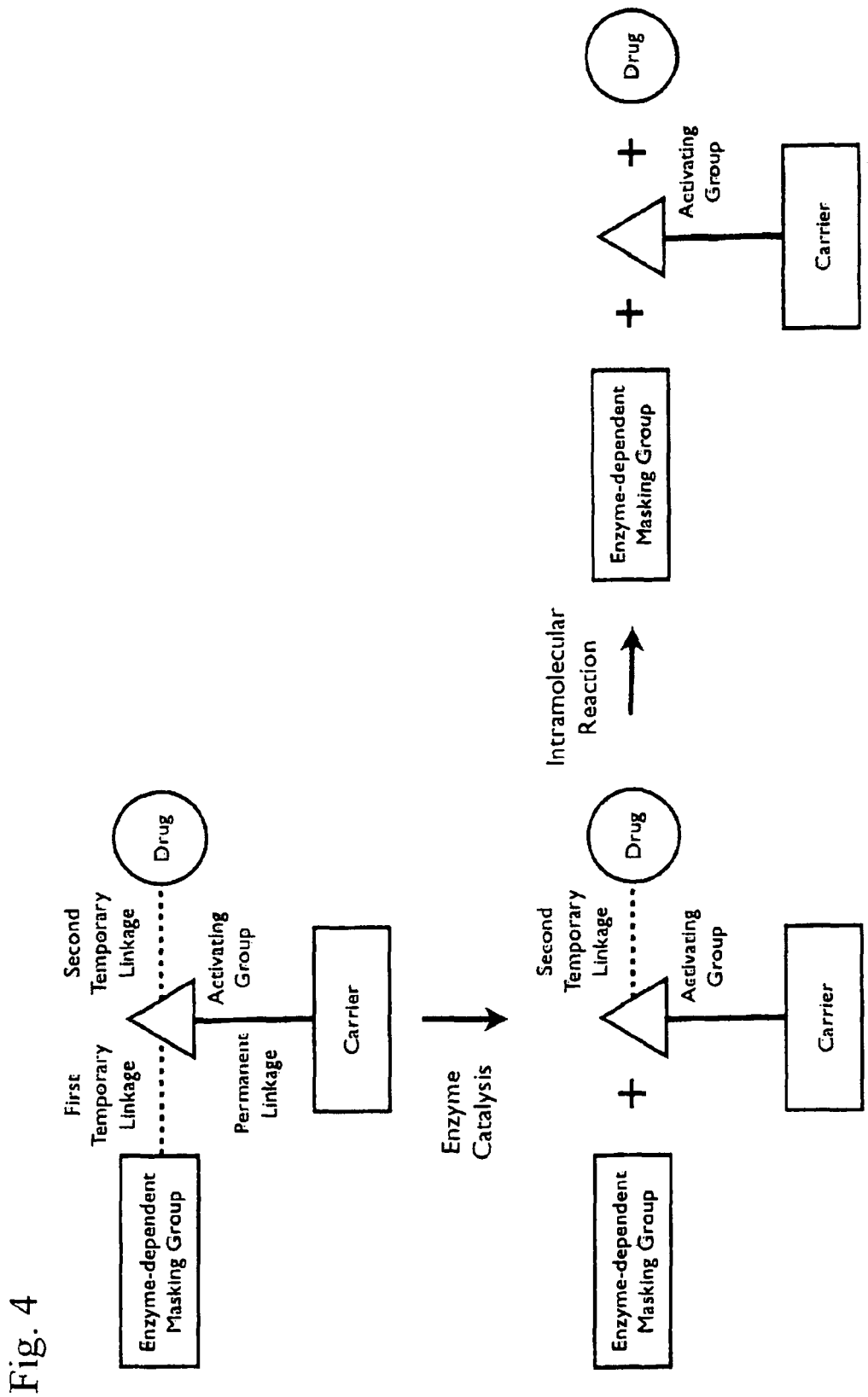
FIG. 4 shows an enzyme-dependent cascade prodrug where the masking group is distinct of the carrier and the carrier is linked permanently to the activating group.
Figure 5:
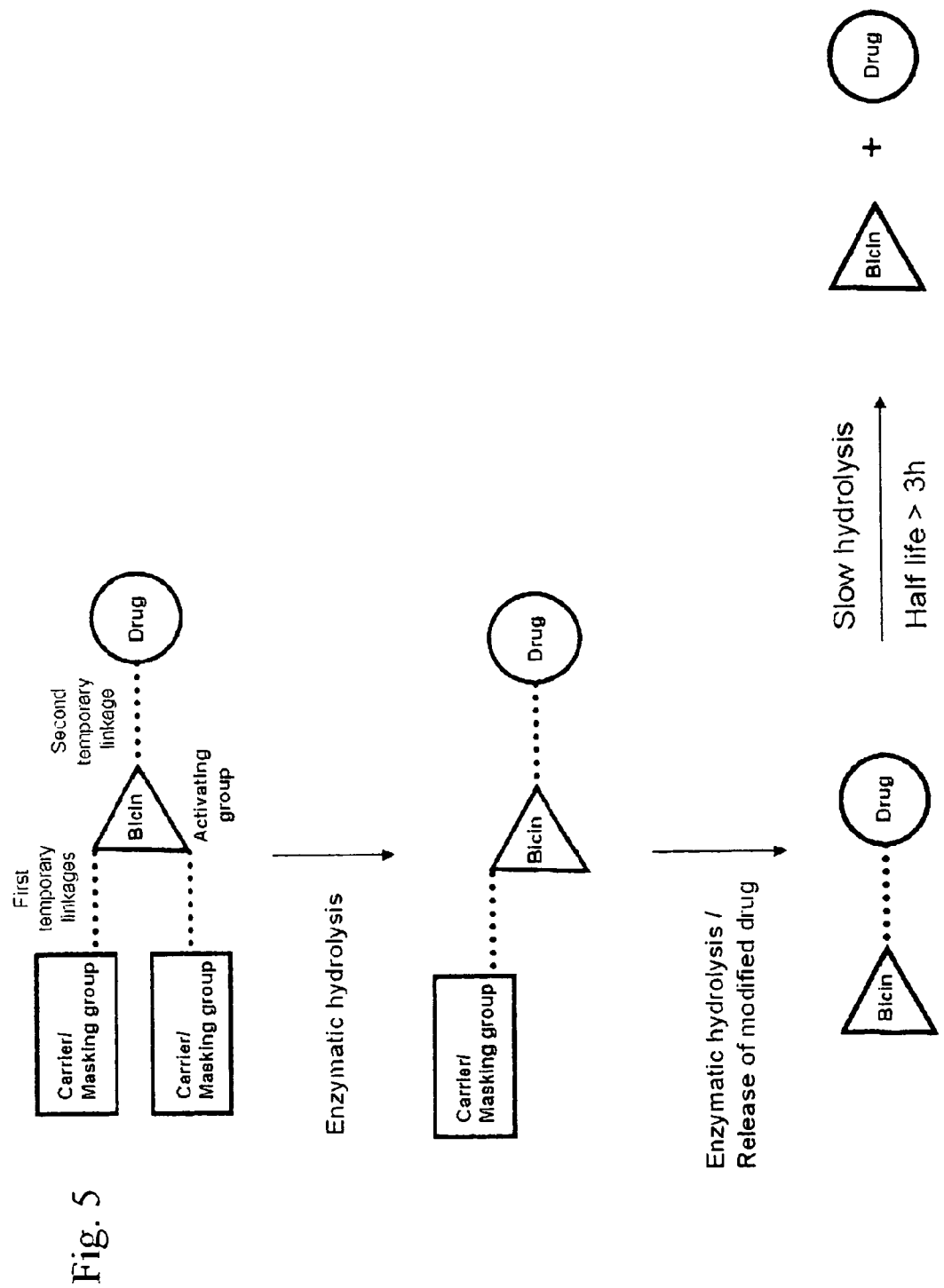
FIG. 5 shows a carrier-linked cascade prodrug with bicine activating group where the masking group is part of the carrier.
Figure 6:
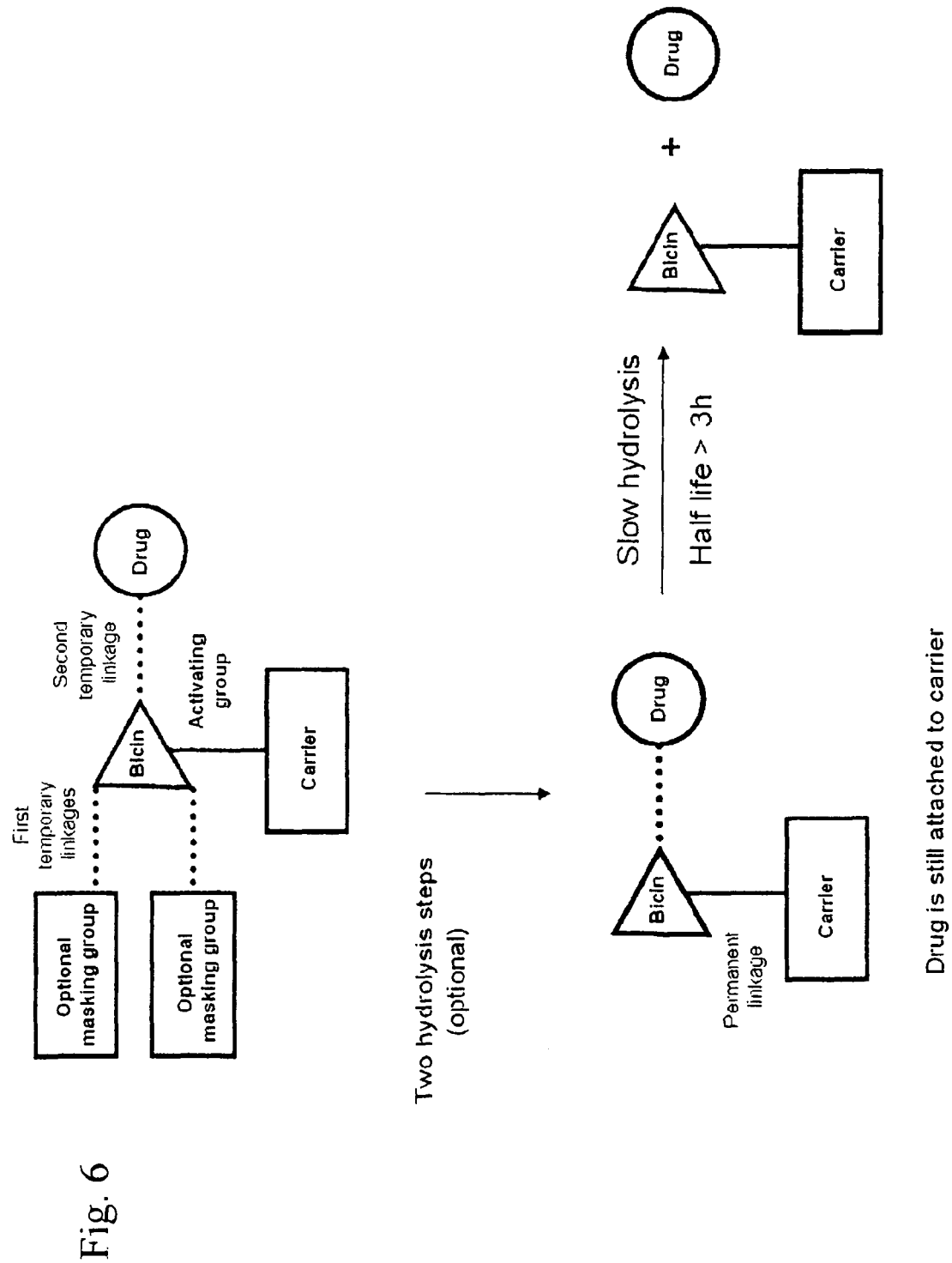
FIG. 6 shows a carrier-linked prodrug with bicine linker where the carrier is linked permanently to the bicine linker.

Fmoc-amino acids, resins and PyBOP were purchased from Novabiochem and are named according to the catalogue. Fmoc-Ado-OH was obtained from Neosystem. All additional chemicals were purchased from Sigma Aldrich. Recombinant human insulin was from ICN Biomedicals (USA). Maleimide-PEG5k was obtained from Nektar (USA). 5-(and-6)-carboxyfluorescein succinimidyl ester (mixed isomers) was obtained from Molecular Probes.

Analysis

Mass spectrometry (MS) was performed on a Waters ZQ 4000 ESI instrument and spectra were, if necessary, interpreted by Waters software MaxEnt.

Size exclusion chromatography was performed using an Amersham Bioscience AEKTAbasic system equipped with a Superdex 200 column (Amersham Bioscience).

Synthesis of 1

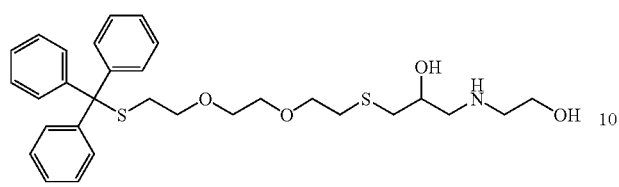

1 g (5.5 mmol) 3,6-Dioxaoctane-1,8-dithiol was dissolved in 10 ml DMF and 1 g (3.6 mmol) tritylchlorid and 1 ml pyridine were added. The solution was stirred at room temperature for 30 min and mono-S-trityl protected 3,6-dioxaoctane-1,8-dithiol was purified by RP-HPLC (yield 850 mg, 2 mmol, 56%).

300 mg (0.71 mmol) S-trityl-3,6-dioxaoctane-1,8-dithiol was dissolved in 5 ml 19/1 (v/v) methanol/water and 300 µl epichlorhydrin, 500 µl pyridine, and 50 µl DIEA were added. The solution was stirred at 40° C. for 14 h and then 50 ml water was added. The precipitate was collected by filtration and dried in vacuo. The precipitate was dissolved in 5 ml dioxane and 100 µl water and 500 µl 2-aminoethanol were added. The solution was stirred at 60° C. for 72 hours. After addition of 1 ml acetic acid product 1 was purified by RP-HPLC (yield: 215 mg, 0.4 mmol, 56%).

MS [M+Na]$^+$=564.9 (MW+Na calculated=564.8 g/mol)

Synthesis of 2

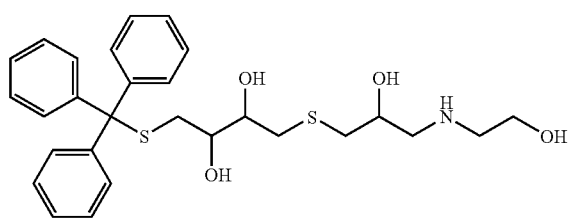

2 was synthesized as described for 1 using 1 g 1,4-dithiothreitol.

MS [M+Na]$^+$=536.8 (MW+Na calculated=536.7 g/mol)

Synthesis of 3 and 4

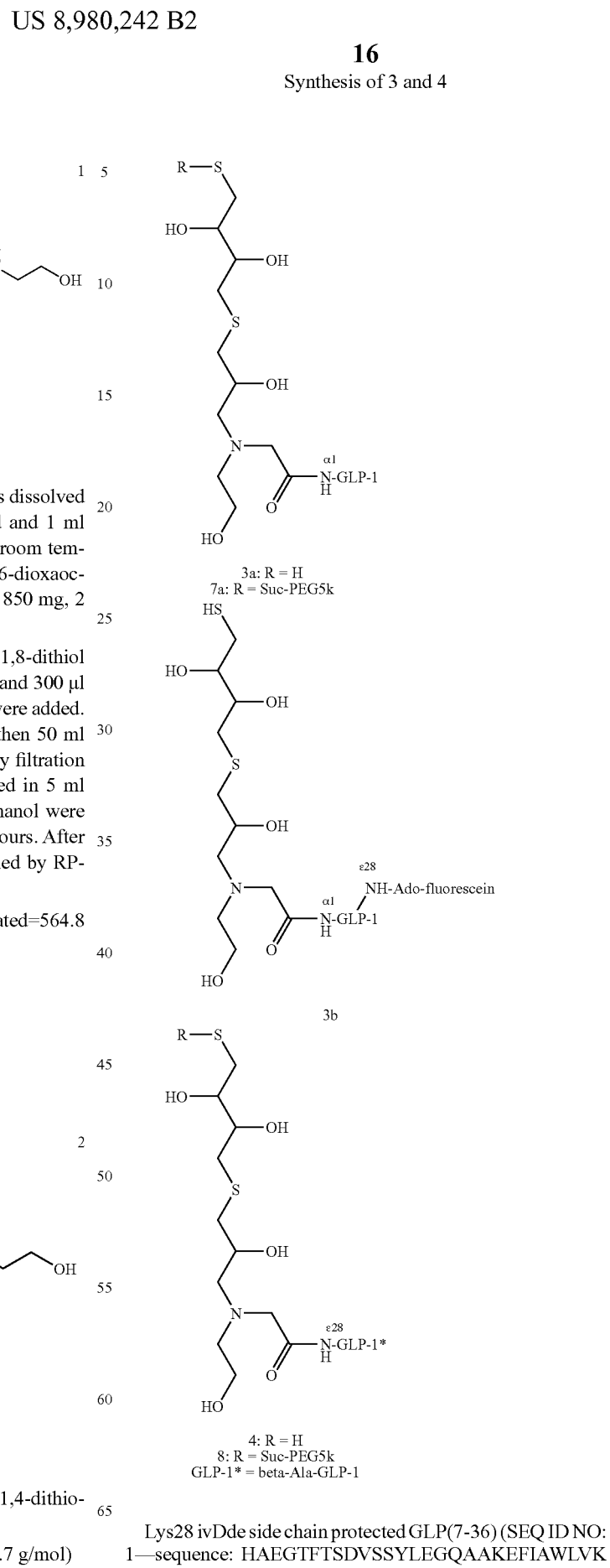

3a: R = H
7a: R = Suc-PEG5k

3b

4: R = H
8: R = Suc-PEG5k
GLP-1* = beta-Ala-GLP-1

Lys28 ivDde side chain protected GLP(7-36) (SEQ ID NO: 1—sequence: HAEGTFTSDVSSYLEGQAAKEFIAWLVK (ivDde)GR-amide) was synthesized on Rink-amide resin employing fmoc-strategy (Specialty Peptide Laboratories, Heidelberg, Germany). N-terminal fmoc-protecting group was removed and the resin was washed with DCM and dried. 50 mg resin (0.11 mmol/g, 5.5 µmol) was suspended in a solution of 42 mg bromoacetic acid (300 µmol) and 47 µl (300 µmol) DIC in 500 µl DMF. The mixture was shaken for 30 min at room temperature. After washing the resin six times with DMF the resin was incubated for 2 h in a solution of 20 mg 2 and 10 µl DIEA in 200 µl DMF. After washing the resin six times with DMF the ivDde protecting group was cleaved by incubating the resin 3 times with 5% hydrazine in DMF for 20 min. Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow. 3a was purified by RP-HPLC and lyophilized. MS: $[M+3H]^{3+}=1204.2$, $[M+2H]^{2+}=1806.3$ (MW calculated=3609 g/mol).

For the synthesis of 3b 150 mg resin (0.11 mmol/g, 16.5 µmol) was suspended in a solution of 126 mg bromoacetic acid (900 µmol) and 141 µl (900 µmol) DIC in 1.5 ml DMF. The mixture was shaken for 30 min at room temperature. After washing the resin six times with DMF the resin was incubated for 2 h in a solution of 60 mg 2 and 30 µl DIEA in 600 µl DMF. After washing the resin six times with DMF the ivDde protecting group was cleaved by incubating the resin 3 times with 5% hydrazine in DMF for 20 min. Resin was washed six times each with DMF.

20 mg Fmoc-8-amino-3,6-dioxaoctanoic acid (50 µmol) was mixed with 8.2 µl DIC (50 µmol), 8 mg HOBt (50 µmol) and 0.5 ml DMF and incubated for 30 min at room temperature. The resin was then incubated with the reaction mixture for 2 h and the resin washed 6 times with DMF. Fmoc protecting group was removed with 20% piperidine in DMF for 15 min. The resin was washed 6 times with DMF and incubated for 1 h with a solution of 12 mg 5-(and-6)-carboxyfluorescein succinimidyl ester (25 µmol) and 10 µl DIEA in 500 µl DMF. The resin was washed six times each with DMF and DCM and dried. Cleavage of the peptide from resin and removal of protecting groups was achieved with 96/2/2 (v/v/v) TFA/triethylsilane/water for 90 min. Volatiles were removed under nitrogen flow. 3b was purified by RP-HPLC and lyophilized.

MS: $[M+3H]^{3+}=1372.0$, $[M+2H]^{2+}=2057.5$ (MW calculated=4113 g/mol)

For the synthesis of 4 50 mg resin (0.11 mmol/g, 5.5 µmol) was suspended in a solution of 25 mg boc-beta alanine (80 µmol) 29 µl DIEA and 42 mg PyBop (80 µmol) in 500 µl DMF. The mixture was shaken for 30 min at room temperature. After washing the resin six times with DMF the ivDde protecting group was cleaved by incubating the resin 3 times with 5% hydrazine in DMF for 20 min. Bromoacetic acid was coupled as described above. After washing the resin six times with DMF the resin was incubated for 14 h in a solution of 20 mg 2 and 10 µl DIEA in 200 µl DMF. Resin was washed six times each with DMF and DCM. Cleavage of the peptide from resin and removal of protecting groups was achieved with 96/2/2 (v/v/v) TFA/triethylsilane/water. Volatiles were removed under nitrogen flow and 4 was purified by RP-HPLC and lyophilized.

MS: $[M+3H]^{3+}=1227.9$, $[M+2H]^{2+}=1841.4$ (MW calculated=3680 g/mol)

Synthesis of 5 and 6

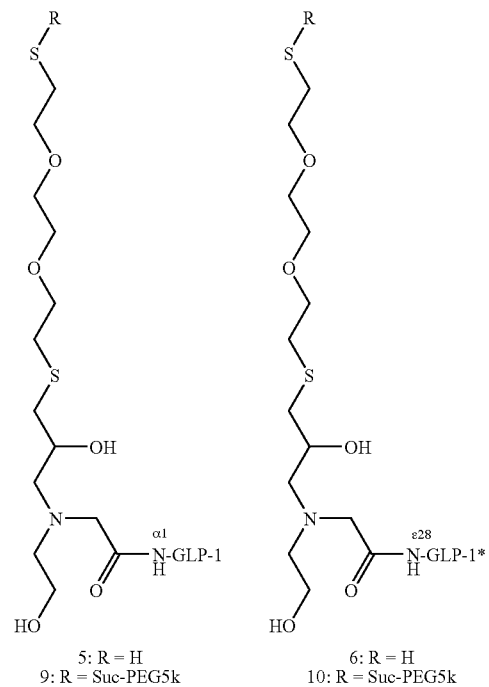

5: R = H
9: R = Suc-PEG5k

6: R = H
10: R = Suc-PEG5k 5 and 6 were synthesized as described for 3 and 4, respectively using 20 mg 1.

5: MS: $[M+3H]^{4+}=1213.4$, $[M+2H]^{3+}=1819.3$ (MW calculated=3637 g/mol)

6: MS: $[M+3H]^{4+}=1237.4$, $[M+2H]^{3+}=1855.2$ (MW calculated=3708 g/mol)

Synthesis Scheme for Compound 14

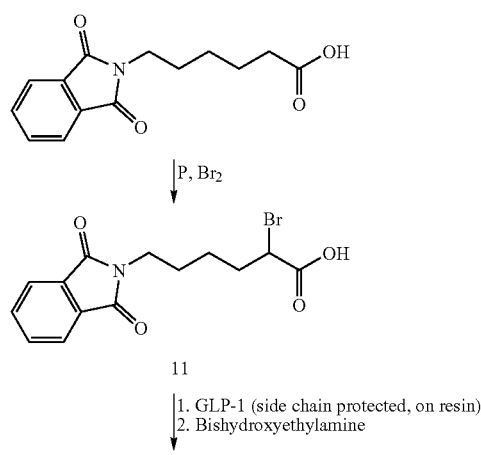

11

1. GLP-1 (side chain protected, on resin)
2. Bishydroxyethylamine

19

-continued

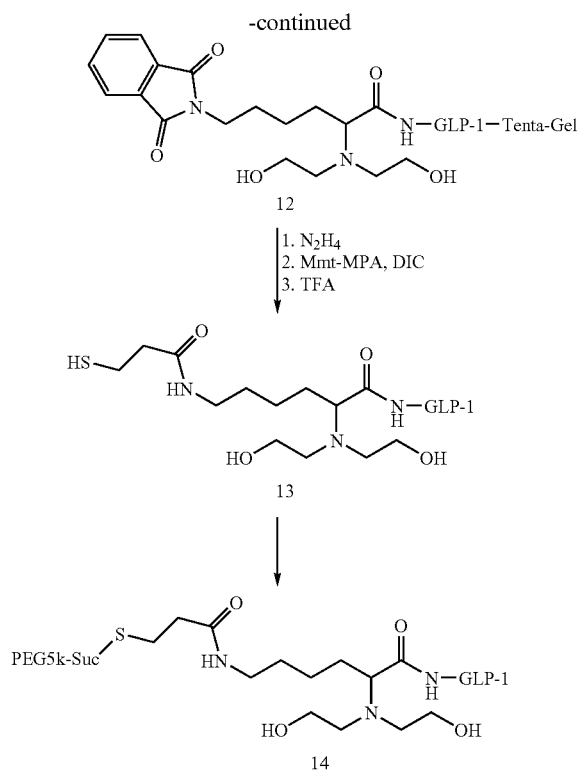

Synthesis of Compound 11

750 mg 6-(1,3-dioxo-1,3-dihydroisoindl-2-yl)hexanoic acid (2.9 mmol) and 180 mg red phosphor (5.8 mmol) were suspended in 7 ml CCl$_4$ and 600 µl Br$_2$ (11.7 mmol) were added in two portions. The reaction mixture was stirred at 90° C. for 5 h. After cooling, the mixture was diluted with 20 ml water and 20 ml diethylether, and neutralized with NaHCO$_3$. Excess Br$_2$ was reduced by addition of NaHSO$_3$. The separated organic layer was extracted with aq. NaHCO$_3$. The aqueous layers were combined and acidified with concentrated HCl. The crude product was collected by filtration and recrystallized from EtOH-water.

Yield 350 mg (36%)

MS [M+Na]$^+$=364.2 (MW+Na calculated=363.0 g/mol)

Synthesis of Compound 13

Side chain protected GLP(7-36) (sequence: HAEGTFTS-DVSSYLEGQAAKEFIAWLVKGR-amide) was synthesized on Rink-amide resin employing fmoc-strategy (Specialty Peptide Laboratories, Heidelberg, Germany). N-terminal fmoc-protecting group was removed and the resin was washed with DCM and dried.

A solution of 3.6 mg 11 (10 µmol), 1.5 mg HOBt (10 µmol), and 1.6 µl DIC (10 µmol) in 300 µl DMF was added to 10 mg loaded resin (0.22 mmol/g, 2.2 µmol) and the mixture was shaken at RT for 3 h. After washing the resin with DMF and DCM a solution of 19 mg bis(2-hydroxyethyl)amine (180 mmol) in 400 ml DMF was added and the suspension was incubated at 70° C. for 2 h to yield 12. The resin was washed with DMF and EtOH and then treated with 400 µl 1/99 (v/v) N$_2$H$_4$ monohydrate/ethanol at 60° C. for 1 h to remove phthalimide protecting group. After washing with EtOH and DMF a solution of 3.8 mg Mmt-mercaptopropionic acid (10 mmol),

20

1.5 mg HOBt (10 µmol), and 1.6 µl DIC (10 µmol) in 300 µl DMF was added and the mixture was shaken at RT for 3 h and subsequently the resin was washed with DMF and DCM; Cleavage of the peptide from resin and removal of protecting groups was achieved with 96/2/2 (v/v/v) TFA/triethylsilane/water. Volatiles were removed under nitrogen flow and 13 was purified by RP-HPLC and lyophilized.

13: Yield 1.2 mg (14%)

MS [M+2H]$^{2+}$=1801.4; [M+3H]$^{3+}$=1201.2 (MW calculated=3604 g/mol)

Synthesis of Conjugates 7, 8, 9, 10, and 14

A solution of 3 (0.1 µmol) in 1/1 (v/v) acetonitrile/water (30 µl) was mixed with maleimide-PEG5k (0.2 µmol) in 1/1 (v/v) acetonitrile/water (50 µl) and 50 µl of 0.5 M phosphate buffer (pH 7.4). The mixture was incubated at RT for 10 min. Conjugate 7 was purified by RP-HPLC and analyzed by SEC (column: Superdex 200, flow rate, 0.75 ml/min) using 10 mM phosphate buffer (pH 7.4), 150 mM NaCl, and 0.005% Tween 20 as mobile phase.

7: SEC retention time: 19.5 min 8, 9, and 10 were synthesized from 4, 5, and 6, respectively, as described above.

14 was synthesized from 13 as described above and purified by SEC (column: Superdex 200, flow rate: 0.75 ml/min) using 10 mM phosphate buffer (pH 7.4), 150 mM NaCl, and 0.005% Tween 20 as mobile phase. The collected eluate (approximately 1.0 ml) was diluted with 0.5 ml buffer containing 0.05% NaN$_3$ and directly used for release rate determination.

14: SEC retention time: 19.7 min

Synthesis Scheme for Compound 17

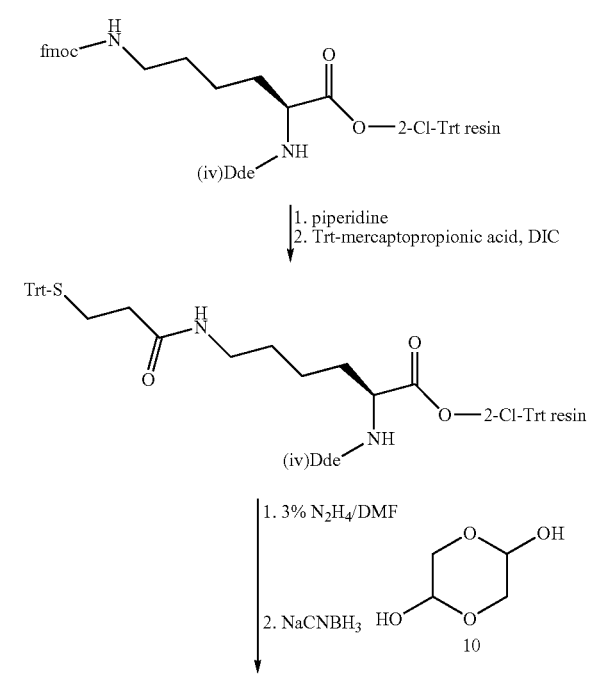

-continued

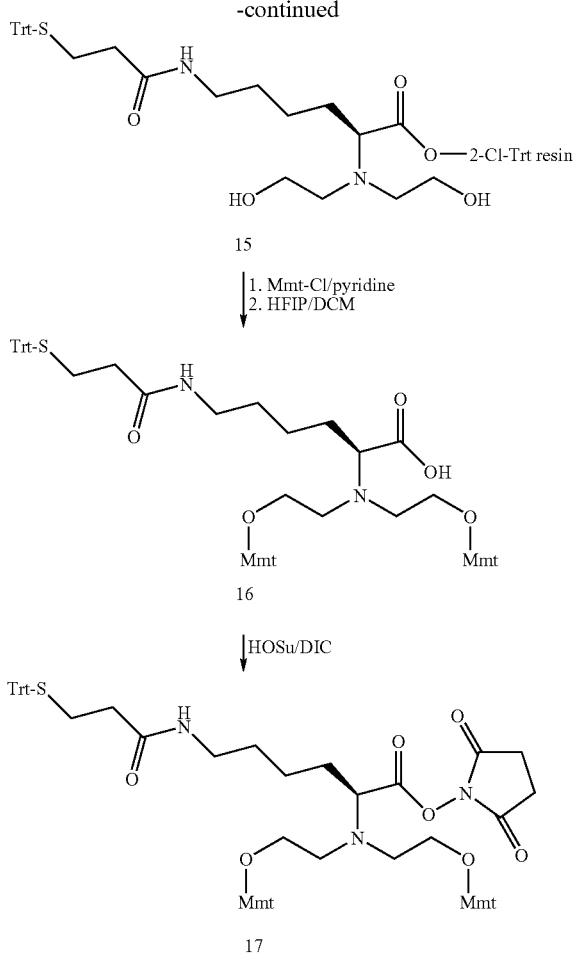

Synthesis of Compound 16

170 mg 2-Chlorotrityl chloride resin (loading 1.2 mmol/g, 0.2 mmol) was incubated for 1.5 h with 200 mg Dde-Lys (Fmoc)-OH (0.4 mmol) and 140 µl DIEA (0.8 mmol) in 4 ml DCM. Fmoc-protecting group was cleaved with piperidine in DMF and the resin was washed with DCM and DMF. The resin was shaken at room temperature for 2 h with a solution of 209 mg Trt-mercaptopropionic acid (0.6 mmol), 93 mg HOBt (0.6 mmol), and 97 µl DIC (0.6 mmol) in DMF. Resin was treated three times with 2% hydrazine in DMF to remove the Dde protecting group. After washing with DMF a solution of 240 mg glycole aldehyde dimer (2.00 mmol), 252 mg NaCNBH$_3$ (4.00 mmol), and 200 µl acetic acid in 20 ml DMF was added and the mixture was shaken overnight to yield 15. Resin was washed with DMF and agitated with 309 mg Mmt-Cl (1.00 mmol) in 2 ml pyridine at RT for 3 h. The resin was washed with DCM and dried. Product 16 was cleaved from resin with 1/7 (v/v) HFIP/DCM (2×2 min) Volatiles were removed under nitrogen flow and 16 was purified by silica gel column chromatography using DCM/MeOH/Et$_3$N (85:15:0.03 (v/v)) as mobile phase.

$R_f$(DCM/MeOH/Et$_3$N (85:15:0.03 (v/v))=0.5
16: Yield 108 mg (50%)
MS [M+Na]$^+$=1131.9 (MW+Na calculated=1131.6 g/mol)

Synthesis of Compound 17

65 mg 16 (59 µmol), 9.3 µl DIC (60 µmol), and 13.8 mg HOSu (120 µmol) in 4 ml acetonitrile were stirred at RT for 3 h. The solvent was evaporated and 17 was purified by silica gel column chromatography using heptane/EtOAc/Et$_3$N (50:50:0.03 (v/v)) as mobile phase.

$R_f$(heptane/EtOAc/Et$_3$N (50:50:0.03 (v/v))=0.4
17: Yield 56 mg (77%) as TFA salt
MS [M+Na]$^+$=1228.7 (MW+Na calculated=1228.6 g/mol)

Synthesis of Compound 18

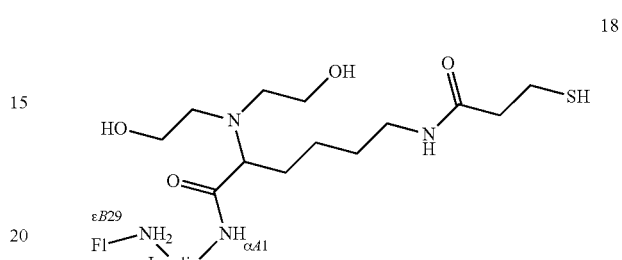

Synthesis of N$^{\epsilon B29}$-Fluorescein Insulin 80 mg (13.8 µmol) rh-insulin were dissolved in 4 ml 1/1 (v/v) DMF/DMSO and 40 µl DIEA were added. 8 mg (17 µmol) 5-(and-6)-carboxyfluorescein succinimidyl ester were added and the solution was stirred for 30 min at room temperature. 4 ml 5/5/1 (v/v/v) acetonitrile/water/acetic acid were added, product N$^{\epsilon B29}$-fluorescein insulin was purified by RP-HPLC and lyophilized. The conjugation site was verified by reduction of N$^{\epsilon B29}$-fluorescein insulin with 1,4-dithiothreitol, protease digestion and MS analysis.

MS: [M+2H]$^{2+}$=3084.0; [M+3H]$^{3+}$=2054.6 (MW calculated=6166 g/mol)

4.4 mg 16 (4.0 µmol), 0.6 µl DIC (4.0 µmol), and 0.9 mg HOSu (8.0 µmol) in DMF (20 µl) were reacted at RT for 2 h. The solution was added to 6.2 mg N$^{\epsilon B29}$-fluorescein-rh-insulin (1.0 µmol) and DIEA (2 µl) in DMSO (60 µl) and the mixture was stirred at RT for 90 min. The reaction mixture was neutralized with acetic acid and diluted with acetonitrile/H$_2$O. RP-HPLC purification gave the appropriate Mmt and Trt-protected intermediate.

After lyophilization, the Mmt- and Trt-protected intermediate was mixed with 95:5 (v/v) TFA/triethylsilane and stirred for 5 min. Volatiles were removed under nitrogen flow and 18 was purified by RP-HPLC and lyophilized.

MS [M+2H]$^{2+}$=3238.2; [M+3H]$^{3+}$=2157.2 (MW calculated=6472 g/mol)

Synthesis of Compound 19

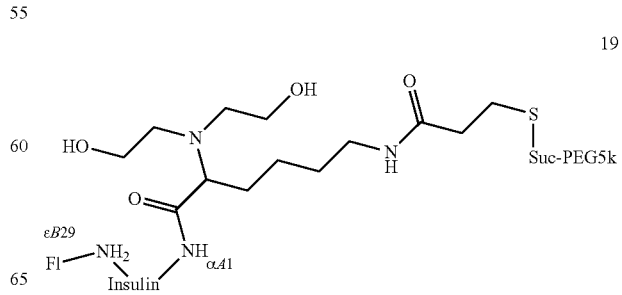

A solution of 18 (1.5 nmol) in 1/4 (v/v) acetonitrile/water (20 µl) was mixed with maleimide-PEG5k (1.9 nmol) in 1/4 (v/v) acetonitrile/water (10 µl) and 50 µl of 0.5 M phosphate buffer (pH 7.4) and incubated at RT for 2 min. Compound was purified by SEC (column: Superdex 200, flow rate: 0.75 mL/min) using 10 mM HEPES buffer (pH 7.4), 150 mM NaCl, 3 mM EDTA, and 0.005% Tween 20 as mobile phase. The collected eluate (approximately 1.5 mL) was directly used for release rate determination.

19: SEC retention time: 18.8 min

Synthesis of $N^{\epsilon B29}$ Conjugated Compound 20

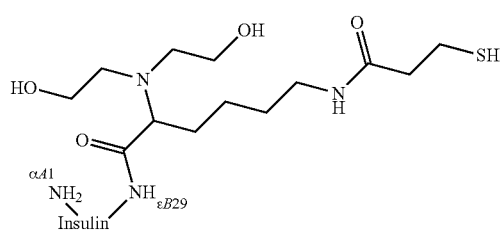

8 µl of 83 mM 17 (0.6 µmol) in NMP was added to 6.2 mg rh-insulin (1.0 µmol) and DIEA (0.5 µl) in DMSO (60 µl) and the mixture was stirred at RT for 90 min. The reaction mixture was neutralized with acetic acid and diluted with acetonitrile/ H₂O. RP-HPLC purification gave the appropriate Trt- and Mmt-protected intermediate.

After lyophilization, the Trt- and Mmt-protected intermediate was mixed with 95:5 (v/v) TFA/triethylsilane and stirred for 5 min. Volatiles were removed under nitrogen flow and 20 was purified by RP-HPLC and lyophilized. Position of insulin modification was verified by DTT reduction and MS analysis.

MS $[M+3H]^{3+}$=2038.1; $[M+4H]^{4+}$=1528.1 (MW calculated=6112 g/mol)

Synthesis of Compound 21

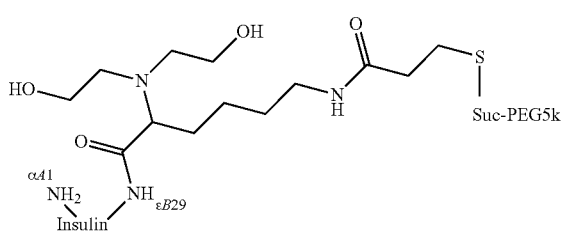

21 was synthesized from 20 as described for 19.
21: SEC retention time: 18.6 min Synthesis of 22

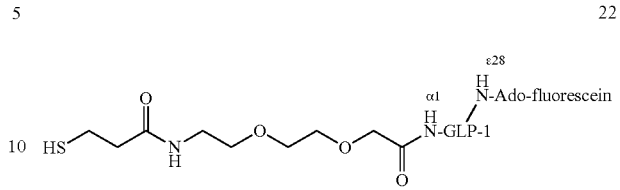

Lys28 ivDde side chain protected GLP(7-36) (SEQ ID NO: 1—sequence: HAEGTFTSDVSSYLEGQAAKEFIAWLVK (ivDde)GR-amide) was synthesized on Rink-amide resin employing fmoc-strategy (Specialty Peptide Laboratories, Heidelberg, Germany). N-terminal fmoc-protecting group was removed and the resin was washed with DCM and dried. 150 mg resin (0.11 mmol/g, 16.5 µmol) was incubated for 1 h in a solution of 20 mg Fmoc-Ado-OH (50 µmol), 25 mg PyBop (50 µmol), and 17 µl DIEA in 500 µl DMF. After fmoc protecting group removal with 96/2/2 DMF/piperidine/DBU the resin was incubated for 1 h with a solution of 17.4 mg Trt-mercaptopropionic acid (50 µmol), 25 mg PyBop (50 µmol), and 17 µl DIEA (100 mop in 500 DMF. ivDde protecting group was removed by incubating the resin in 500 µl 9/1 (v/v) DMF/hydrazine for 2 h. After washing the resin with DMF, Fmoc-Ado-OH was coupled and finoc protecting group was removed as described above. The resin was then incubated 2 h with a solution of 16 mg 5-(and-6)-carboxyfluorescem-succinimidyl ester and 6 µl DIEA in 500 ml DMF. Cleavage of the peptide from resin and removal of protecting groups was achieved with 96/2/2 (v/v/v) TFA/triethylsilane/ water for 90 min. Volatiles were removed under nitrogen flow. 22 was purified by RP-HPLC and lyophilized.

MS: $[M+3H]^{3+}$=1345.9, $[M+2H]^{2+}$=2016.9 (MW calculated=4034 g/mol)

Synthesis of rHSA-Maleimide (23)

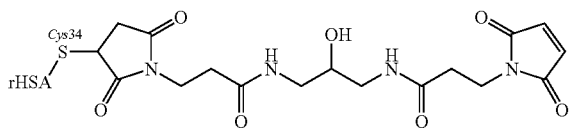

500 µl 3 mM rHSA (1.5 µmol) solution in 145 mM NaCl, 32 mM sodium octanoate, 0.0015% Tween-80 was mixed with 100 µl 0.5 M phosphate buffer pH 7.0. 1.5 mg N,N'-bismaleimidopropionyl-2-hydroxy-1,3-diaminopropane (3.75 µmol) were added and the mixture was reacted for 20 min at RT. Compound 23 was purified by SEC (column: Superdex 200 26/60, flow rate: 4 ml/min) using 10 mM sodium phosphate buffer pH 7.4, 150 mM NaCl as mobile phase.

ESI-MS=66900 (MW calculated=66864 g/mol)

Synthesis of Bodipy Labelled rHSA (24)

500 µl 3 mM rHSA (1.5 µmol) solution in 145 mM NaCl, 32 mM sodium octanoate, 0.0015% Tween-80 was mixed with 250 µl 0.5 M sodium borate buffer pH 8.0. 43 µl 100 mM BODIPY® TR-X, STP ester (Molecular Probes) in DMSO were added and the mixture was reacted for 20 min at RT. Bodipy labeled rHSA (24) was purified by SEC (column: Superdex 200 26/60, flow rate: 4 ml/min) using 10 mM sodium phosphate buffer pH 7.4, 150 mM NaCl as mobile phase.

Synthesis of 25

25

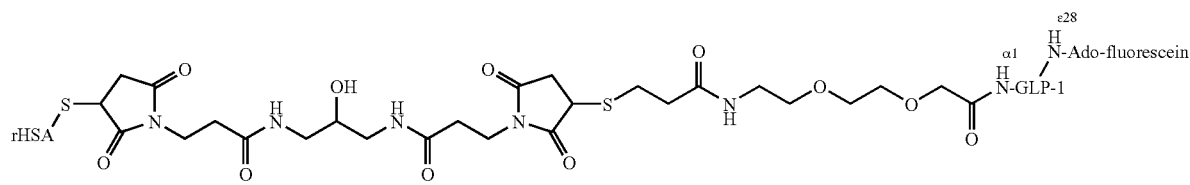

45 mg 23 in 0.75 ml 10 mM sodium phosphate 150 mM NaCl pH 6 were mixed with 250 µl 0.5 ml sodium borate pH 8 and 8 mg 22 in 50 µl DMSO were added. The solution was incubated for 20 min at room temperature. 25 was purified by SEC (column: Superdex 200 26/60, flow rate: 4 ml/min) using 10 mM sodium phosphate buffer pH 7.4, 150 mM NaCl as mobile phase.

MS: 70870 (MW calculated=70898 g/mol)

Synthesis of 26 kinetics and to control for injection site variability an internal standard was used. This internal standard was provided by co-injecting unconjugated bodipy labeled rHSA (24).

Figure 7:
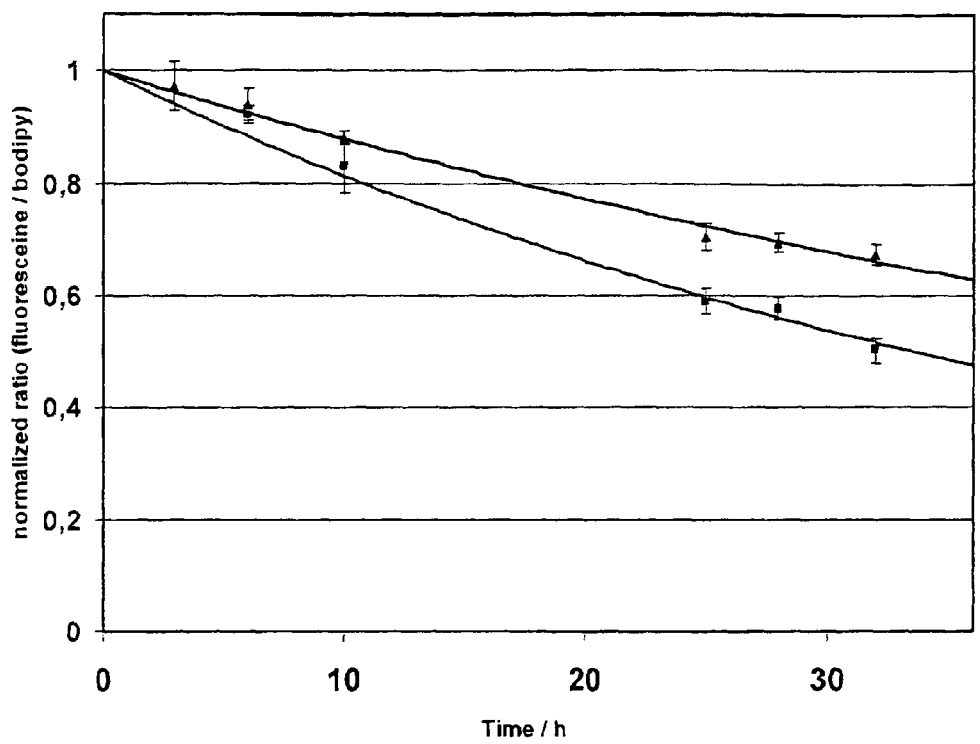
FIG. 7 shows in vivo cleavage of polymeric prodrugs.
Figure 8:
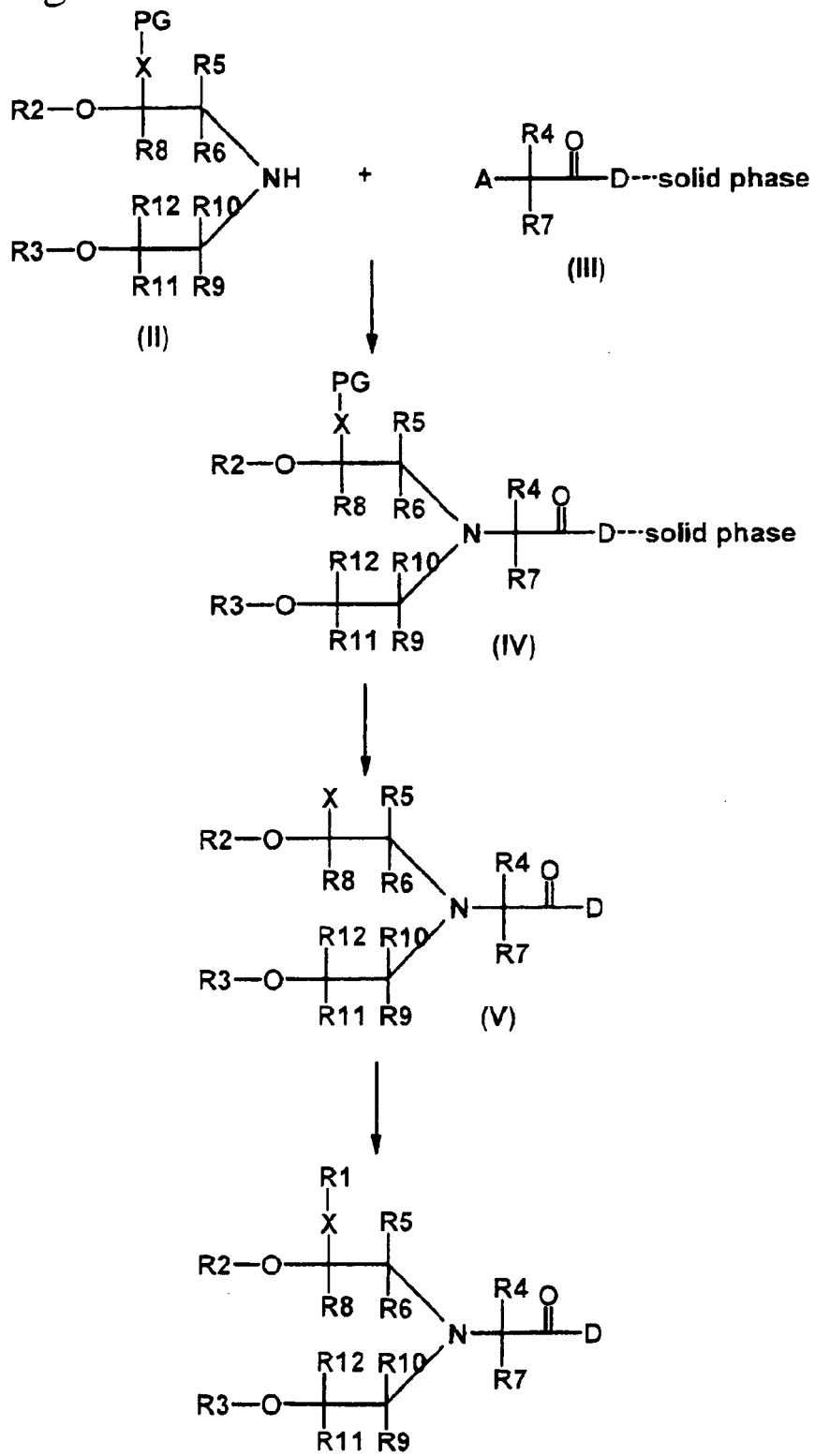
FIG. 8 shows general synthesis methods.
Figure 9:
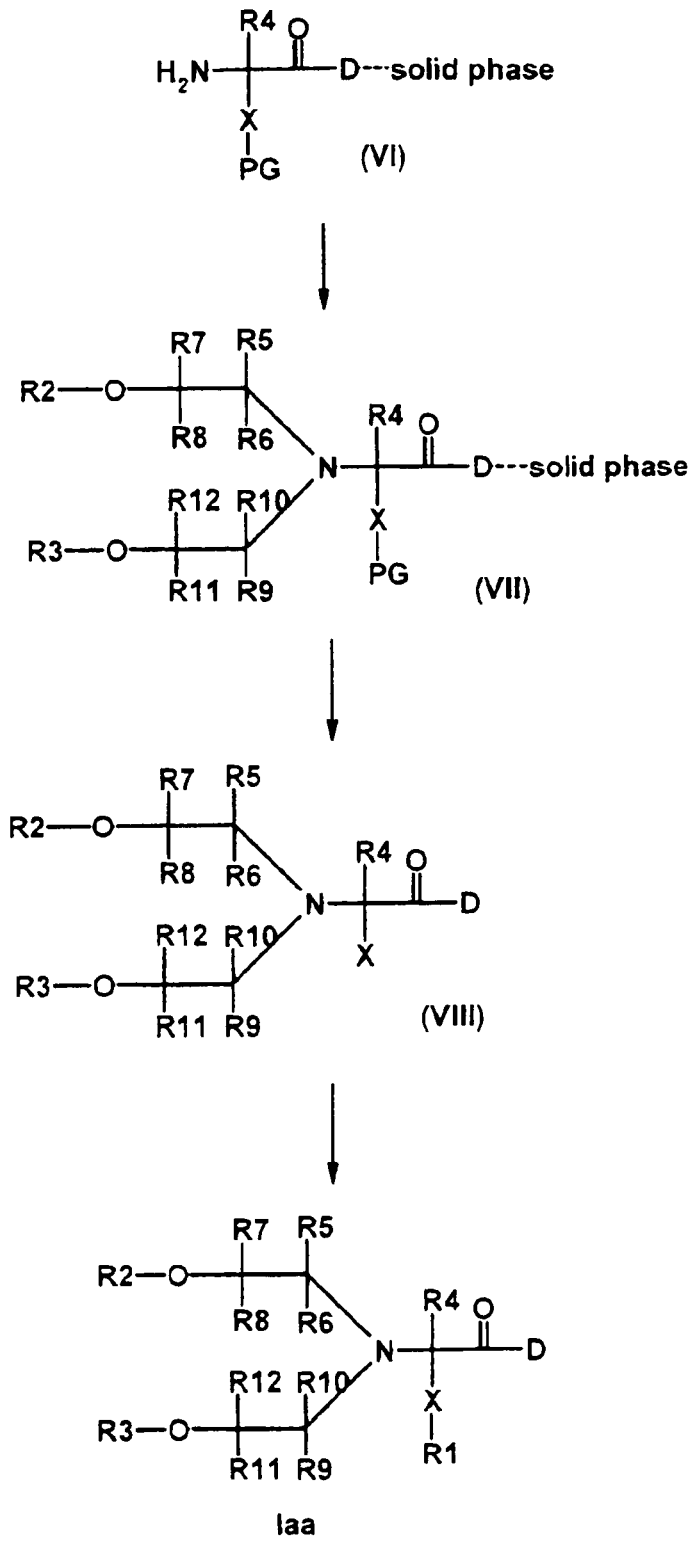
FIG. 9 shows general synthesis methods.
Figure 10:
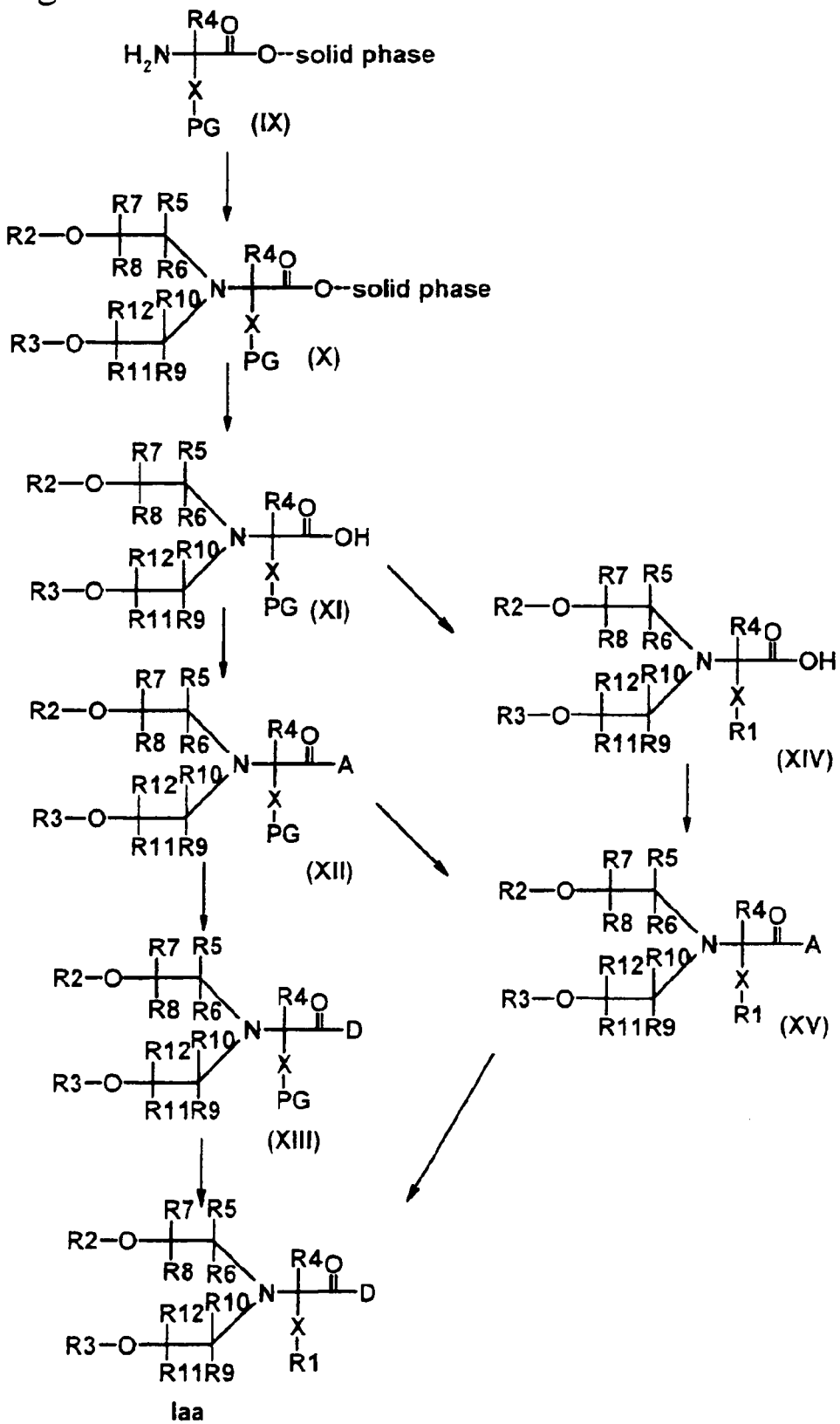
FIG. 10 shows general synthesis methods.

In the control experiment a group of five male Sprague Dawley rats was used. A mixture of 56 nmol 25 and 97 nmol 24 in 450 µl 10 mM sodium phosphate pH 7.4, 150 mM NaCl was injected subcutaneously into each rat. Plasma samples were taken at time intervals and fluorescein and Bodipy fluorescence was measured. Normalized ratios of fluorescein/Bodipy fluorescence over time were plotted (FIG. 7, triangles).

In the main experiment a group of three male Sprague Dawley rats was used. A mixture of 40 nmol 26 and 72 nmol 24 in 450 µl 10 mM sodium phosphate pH 7.4, 150 mM NaCl was injected subcutaneously into each rat. Plasma samples were taken at the same time intervals as in the control experiment and fluorescein and Bodipy fluorescence was measured. Normalized ratios of fluorescein/Bodipy fluorescence over time were plotted (FIG. 7, squares).

26

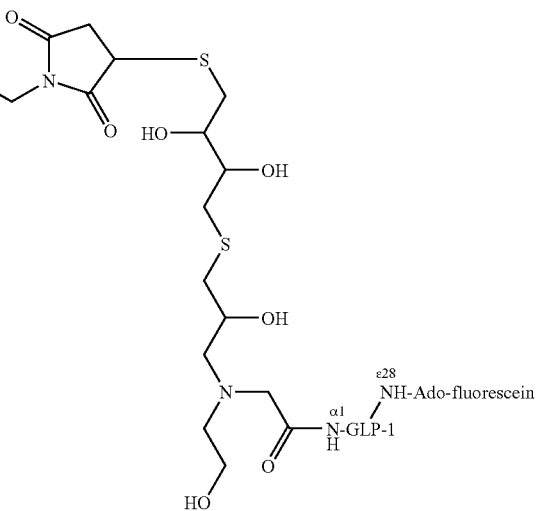

26 was synthesized as described for 25 using 23 and 3b.
MS: 70950 (MW calculated=70977 g/mol)

Release of Fluorescein-GLP-1 from rHSA Conjugate 26 In Vivo

Release of fluorescein-GLP-1 from rHSA conjugate 26 in vivo was measured subtractively, by determining the amount of fluorescein-GLP-1 remaining attached to the conjugate after injection into rat. This was accomplished by comparing two different rHSA-fluorescein-GLP-1 conjugates, one in which fluorescein-labeled GLP-1 was attached to albumin with a reversible linker (conjugate 26), and a control construct in which labeled GLP-1 was attached to rHSA permanently (conjugate 25). In order to obtain highly accurate in vivo The data obtained in the main experiment divided by the data obtained in the control experiment plotted over time gives the release kinetics of fluorescein-GLP-1 from conjugate 26.

Release of Peptide or Fluorescein-Peptide from Conjugates in Buffer pH 7.4

Release of (fluorescein)-peptide from (fluorescein)-peptide conjugates 7, 8, 9, 10, 14, 19, 21, and 26 was effected by linker hydrolysis in aqueous buffer pH 7.4. Lyophilized conjugates were dissolved in 10 mM HEPES buffer (pH 7.4), 150 mM NaCl, 3 mM EDTA, and 0.005% Tween 20. Redissolved conjugates and collected SEC eluates of (fluorescein) peptide conjugates were incubated at 37° C. and samples were taken at time intervals and analyzed by RP-HPLC (peptide conjugates) and UV detection at 215 nm or SEC (fluorescein peptide conjugates) and detection at 500 nm. Peaks correlating with the retention time of native peptide or fluorescein-peptide, respectively, were integrated and plotted against incubation time, and curve-fitting software was applied to estimate the corresponding halftime of release.

| compound | $t_{1/2}$ buffer pH 7.4 | $t_{1/2}$ in vivo |
|---|---|---|
| 7 | 6 d | nd |
| 8 | 9 d | nd |
| 9 | 10 d | nd |
| 10 | 11 d | nd |
| 14 | 12 d | nd |

MS mass spectrum
MW molecular mass
Npys 3-nitro-2-pyridinesulfenyl
PyBOP benzotriazole-1-yl-oxy-tris-pyrrolidino-phosphonium hexafluorophosphate
rHSA recombinant human serum albumin
RP-HPLC reversed-phase high performance liquid chromatography
RT room temperature
SEC size exclusion chromatography
Suc succinimidopropionyl
TES triethylsilane
TFA trifluoroacetic acid
THF tetrahydrofurane
UV ultraviolet
VIS visual

```
                         SEQUENCE LISTING

<160> NUMBER OF SEQ ID NOS: 1

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

-continued

| compound | $t_{1/2}$ buffer pH 7.4 | $t_{1/2}$ in vivo |
|---|---|---|
| 19 | 22 d | nd |
| 21 | 74 d | nd |
| 26 | 6 d | 3.75 d |

ABBREVIATIONS

Ado 8-amino-3,6-dioxaoctanoic acid
Boc t-butyloxycarbonyl
Bodipy BODIPY® TR-X
DBU 1,3-diazabicyclo[5.4.0]undecene
DCM dichloromethane
(iv)Dde 1-(4,4-dimethyl-2,6-dioxo-cyclohexyliden)3-methyl-butyl
DIC diisopropylcarbodiimide
DIEA diisopropylethylamine
DMAP dimethylamino-pyridine.
DMF N,N-dimethylformamide
DMSO dimethylsulfoxide
DSC disuccinidylcarbonate
EDTA ethylenediaminetetraacetic acid
eq stoichiometric equivalent
fmoc 9-fluorenylmethoxycarbonyl
Fmoc-Ado-OH Fmoc-8-amino-3,6-dioxaoctanoic acid
HFIP hexafluoroisopropanol
HEPES N-(2-hydroxyethyl) piperazine-N'-(2-ethanesulfonic acid)
HOBt N-hydroxybenzotriazole
LCMS mass spectrometry-coupled liquid chromatography
Mal maleimidopropionyl
Mmt 4-methoxytrityl

The invention claimed is:

1. A polymeric prodrug comprising:
   at least one polymer attached via at least one permanent bond to a bicine linker, the bicine linker being attached via a temporary linkage to an amine containing biologically active moiety;
   wherein the prodrug has the following structure:

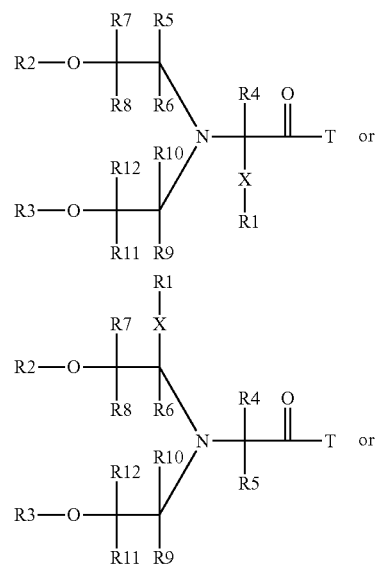

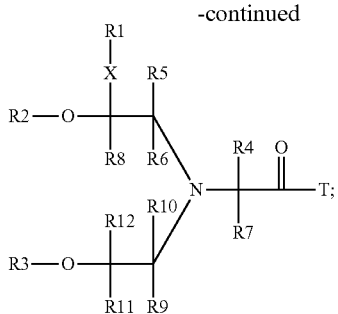

and
wherein:
T is D;
D is a residue of an amine containing biologically active moiety;
X is a spacer moiety;
R2 and R3 are independently selected from the group consisting of hydrogen, acyl groups, and protecting groups for hydroxyl groups;
R4 to R12 are independently selected from the group consisting of hydrogen, X—R1, substituted and non-substituted linear, branched and cyclical $C_1$ to $C_8$ alkyls and heteroalkyls, aryls, substituted aryls, substituted and nonsubstituted heteroaryls, cyano, nitro, halogen, carboxy, and carboxamide; and
R1 is a polymer.

2. The prodrug of claim 1;
wherein the biologically active moiety is selected from the group consisting of small molecule biologically active agents and biopolymers.

3. The prodrug of claim 2;
wherein the biologically active moiety is a biopolymer selected from the group consisting of proteins, polypeptides, oligonucleotides, and peptide nucleic acids.

4. The prodrug of claim 3;
wherein the biopolymer is a polypeptide selected from the group consisting of ACTH, adenosine deaminase, agalsidase, albumin, alpha-1 antitrypsin (AAT), apha-1 proteinase inhibitor (API), alteplase, anistreplase, ancrod serine protease, antibodies (monoclonal and polyclonal, and fragments and fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idurnonidase, immune globulins, influenza vaccines, interleukins (1 alpha, 1 beta, 2, 3, 4, 6, 10, 11, 12), IL-1 receptor antagonist (rhIL-1ra), insulins, interferons (alpha 2a, alpha 2b, alpha 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines, and plant protein.

5. The prodrug of claim 3;
wherein the biopolymer is a protein prepared by recombinant DNA technology.

6. The prodrug of claim 3;
wherein the biopolymer is a protein selected from the group consisting of antibody fragments, single chain binding proteins, catalytic antibodies, and fusion proteins.

7. The prodrug of claim 3;
wherein the biopolymer is a protein selected from the group consisting of antibodies, calcitonin, G-CSF, GM-CSF, erythropoietin, hemoglobins, interleukins, insulins, interferons, SOD, somatropin, TNF, TNF-receptor-IgG Fc, and glucagon-like peptides.

8. The prodrug of claim 2;
wherein the biologically active moiety is a small molecule biologically active agent selected from the group consisting of central nervous system-active agents, anti-infective, anti-neoplastic, antibacterial, anti-fungal, analgesic, contraceptive, anti-inflammatory, steroidal, vasodilating, vasoconstricting, and cardiovascular agents with at least one primary or secondary amino group.

9. The prodrug of claim 2;
wherein the biologically active moiety is a small molecule biologically active agent selected from the group consisting of daunorabicin, doxorubicin, idarubicin, mitoxantron, aminoglutethimide, amantadine, diaphenylsulfon, ethambutol, sulfadiazin, sulfamerazin, sulfamethoxazol, sulfalen, clinafioxacin, moxifloxacin, ciprofloxaxin, enoxacin, norfloxacin, neomycin B, sprectinomycin, kanamycin A, meropenem, dopamin, dobutamin, lisinopril, serotonin, acivicin and carbutamid.

10. The prodrug of claim 1;
wherein R4 to R12 are independently selected from hydrogen, and substituted and non-substituted linear, branched and cyclical $C_1$ to $C_8$ alkyls and heteroalkyls.

11. The prodrug of claim 1;
wherein R1 is selected from the group consisting of polyalkyloxy-based polymers, dextran, chitosan, hyaluronic acid and derivatives, alginate, xylan, mannan, carrageenan, agarose, cellulose, starch, hydroxyethyl starch (HES) and other carbohydrate-based polmers, poly(vinyl alcohols), poly(oxazolines), poly(anhydrides), poly(ortho esters), poly(carbonates), poly(urethanes), poly(acrylic acids), poly(acrylamides), poly(acrylates), poly(methacrylates), poly(siloxanes), poly(vinylpyrrolidone), poly(cyanoacrylates), poly(esters), poly(iminocarbonates), poly(amino acids), collagen, gelatin, copolymers, grafted copolymers, cross-linked polymers, and block copolymers from the above listed polymers.

12. The prodrug of claim 1;
wherein R1 is a hydrogel.

13. The prodrug of claim 1;
wherein R1 is a branched or hyperbranched polymer.

14. The prodrug of claim 1;
wherein R1 is a dendrimer or dense star polymer.

15. The prodrug of claim 1;
wherein R1 is a biopolymer.

16. The prodrug of claim 1;
herein wherein R1 is a protein.
17. The prodrug of claim 3;
wherein the protein is albumin, an antibody, fibrin, casein or any other plasma protein.
18. The prodrug of claim 1;
wherein R1 further includes one or more biologically active substances.
19. The prodrug of claim 1;
wherein R1 has at least one functional group for linkage to X.
20. The prodrug of claim 19;
wherein the at least one functional group is selected from the group consisting of carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl, arylating agents, hydroxylamine, disulfides, vinyl sulfone, vinyl ketone, diazoalkanes, diazoacetyl compounds, epoxide, oxirane, and aziridine.
21. The prodrug of claim 19;
wherein the at least one functional group is selected from the group consisting of thiol, maleimide, amino, carboxylic acid and derivatives, carbonate and derivatives, carbamate and derivatives, aldehyde, and haloacetyl.
22. The prodrug of claim 1;
wherein the bond or group formed between X and R1 is selected from the group consisting of disulfide, S-succinimido, amide, amino, carboxylic ester, sulphonamide, carbamate, carbonate, ether, thioether, imine, oxime, hydrazone, urea, thiourea, phosphate, and phosphonate.
23. The prodrug of claim 1;
wherein the bonds or groups formed between X and R1 is selected from the group consisting of S-succinimido, amide, carbamate, thioether, and urea.
24. A method for the synthesis of a polymeric prodrug of claim 1, comprising:
providing a starting molecule of Formula III:

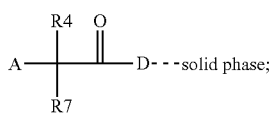

(III)

displacing A with a starting molecule of Formula II:

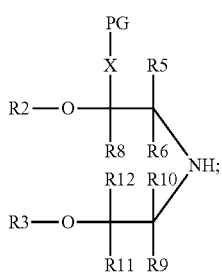

(II)

cleaving the resulting intermediate from the solid phase and cleaving all present protecting groups to form an intermediate of Formula V:

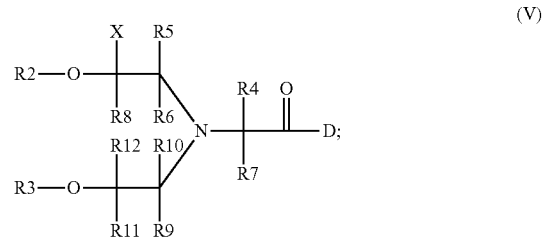

(V)

and attaching a polymer R1 to X in the intermediate of Formula V to form the polymeric prodrug of claim 1;
wherein:
D is a residue of an amine containing biologically active moiety;
X is a spacer moiety;
R2 and R3 are independently selected from the group consisting of hydrogen, acyl groups, and protecting groups for hydroxyl groups;
R4 to R12 are independently selected from the group consisting of hydrogen, X—R1, substituted and non-substituted linear, branched and cyclical $C_1$ to $C_8$ alkyls and heteroalkyls, aryls, substituted aryls, substituted and nonsubstituted heteroaryls, cyano, nitro, halogen, carboxy, and carboxamide; and
R1 is a polymer.

25. A method for the synthesis of a polymeric prodrug of claim 1, comprising:
providing a starting molecule of Formula VI:

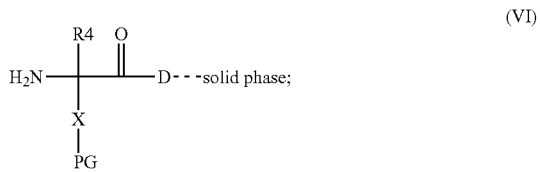

(VI)

forming an intermediate of Formula VII by at least one substitution or reductive alkylation step, where the Formula VII is:

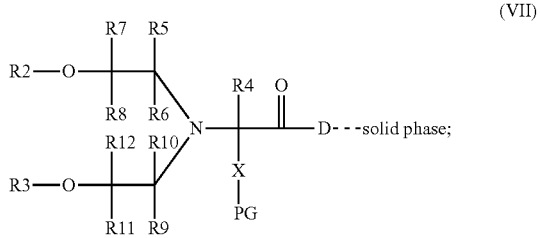

(VII)

cleaving the intermediate of Formula II from the solid phase and cleaving all present protecting groups to form an intermediate of Formula VIII:

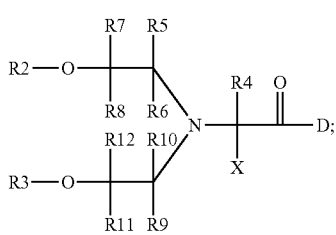

(VIII)

and attaching a polymer R1 to X in the intermediate of Formula VII to form the polymeric prodrug of claim 1;

wherein:

D is a residue of an amine containing biologically active moiety;

X is a spacer moiety;

R2 and R3 are independently selected from the group consisting of hydrogen, acyl groups, and protecting groups for hydroxyl groups;

R4 to R12 are independently selected from the group consisting of hydrogen, X—R1, substituted and non-substituted linear, branched and cyclical $C_1$ to $C_8$ alkyls and heteroalkyls, aryls, substituted aryls, substituted and nonsubstituted heteroaryls, cyano, nitro, halogen, carboxy, and carboxamide; and R1 is a polymer.

26. A method for the synthesis of a polymeric prodrug of claim 1, comprising:

providing a starting molecule of Formula IX:

(IX)

$H_2N-\overset{R4}{\underset{\underset{PG}{X}}{C}}-\overset{O}{\overset{\|}{C}}-O---\text{solid phase};$ forming an intermediate of Formula X by at least one substitution or reductive alleviation step, where Formula X is:

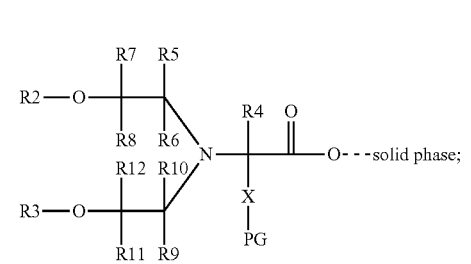

(X)

cleaving the intermediate of Formula X from the solid phase without cleaving all present protecting groups to form an intermediate of Formula XI:

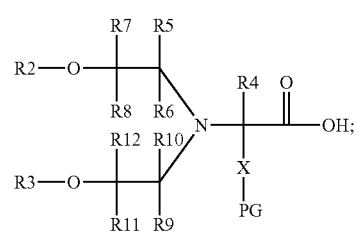

(XI)

activating intermediate of Formula XI with a activating reagent to form an intermediate of Formula XII:

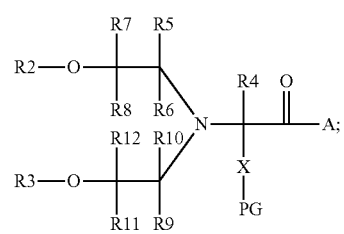

(XII)

reacting intermediate of Formula XII with an amine containing drug D to form an intermediate of Formula XIII, and

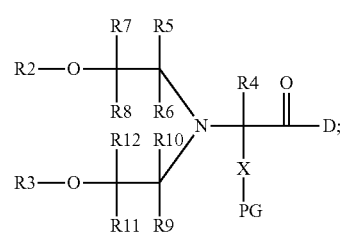

(XIII)

and attaching a polymer R1 to X in the intermediate of Formula XIII after cleavage of the protecting group PG to form the polymeric prodrug of claim 1;

wherein:

D is a residue of an amine containing biologically active moiety;

A is a leaving group;

X is a spacer moiety;

R2 and R3 are independently selected from the group consisting of hydrogen, acyl groups, and protecting groups for hydroxyl groups;

R4 to R12 are independently selected from the group consisting of hydrogen, X—R1, substituted and non-substituted linear, branched and cyclical $C_1$ to $C_8$ alkyls and heteroalkyls, aryls, substituted aryls, substituted and nonsubstituted heteroaryls, cyano, nitro, halogen, carboxy, and carboxamide; and R1 is a polymer.

27. A method for the synthesis of a polymeric prodrug of claim 1, comprising:

providing a starting molecule of Formula XI:

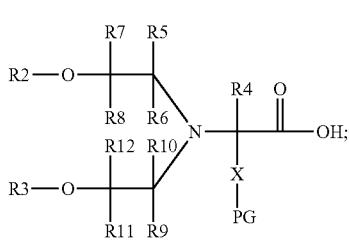

attaching a polymer R1 to X in the intermediate of Formula XI after cleavage of the protecting group PG to form an intermediate of formula XIV:

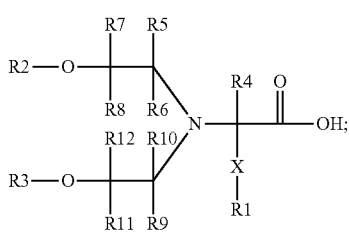

activating intermediate of Formula XIV with a activating reagent to form a polymeric prodrug reagent of Formula XV:

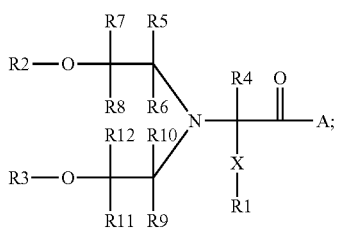

and
reacting intermediate of Formula XV with an amine containing drug D to form the polymeric prodrug of claim 1;
wherein:
D is a residue of an amine containing biologically active moiety;
A is a leaving group;
X is a spacer moiety;
R2 and R3 are independently selected from the group consisting of hydrogen, acyl groups, and protecting groups for hydroxyl groups;
R4 to R12 are independently selected from the group consisting of hydrogen, X—R1, substituted and non-substitutedlinear, branched and cyclical $C_1$ to $C_8$ alkyls and heteroalkyls, aryls, substituted aryls, substituted and nonsubstituted heteroaryls, cyano, nitro, halogen, carboxy, and carboxamide; and
R1 is a polymer.

28. A method for the synthesis of a polymeric prodrug of claim 1, comprising:

providing a starting molecule of Formula XII:

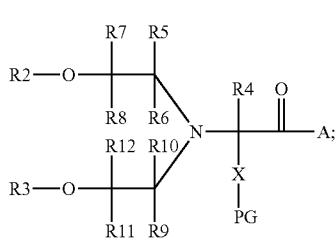

attaching a polymer R1 to X in the intermediate of Formula XII after cleavage of the protecting group PG to form a polymeric linker reagent of formula XV:

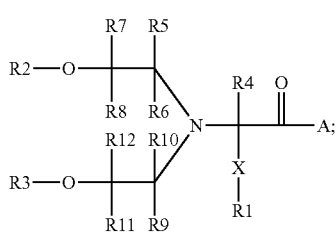

and
reacting the intermediate of Formula XV with an amine containing drug D to form the polymeric prodrug of claim 1;
wherein:
D is a residue of an amine containing biologically active moiety;
A is a leaving group;
X is a spacer moiety;
R2 and R3 are independently selected from the group consisting of hydrogen, acyl groups, and protecting groups for hydroxyl groups;
R4 to R12 are independently selected from the group consisting of hydrogen, X—R1, substituted and non-substituted linear, branched and cyclical $C_1$ to $C_8$ alkyls and heteroalkyls, aryls, substituted aryls, substituted and nonsubstituted heteroaryls, cyano, nitro, halogen, carboxy, carboxamide; and
R1 is a polymer.

29. The method of claim 26;
wherein the activating agent is a carbodiimide N-hydroxysuccinimide mixture.

30. The method of claim 26;
wherein A is selected from the group consisting of chloride, bromide, fluoride, nitrophenoxy, imidazolyl, N-hydroxysuccinimidyl, N-hydroxybenzotriazolyl, N-hydroxylazobenzotriazolyl, pentafluorphenoxy, and N-hydroxysulfosuccinimidyl.

31. A method for hydrolysing the prodrug of claim 1, comprising:
a step of placing the prodrug in solution with a pH of approximately 7.4.

32. The method of claim 31;
wherein the solution is an extra-cellular fluid.

33. A method of administration of an amine-containing moiety to a living organism comprising:
a first step of providing a polymeric prodrug according to claim 1;
a second step of administering the polymeric prodrug to the living organism; and a third step of cleaving the amine-containing moiety from the polymeric prodrug by means of a substantially non-enzymatic reaction.

34. The method of claim 33;
wherein the amine-containing moiety is a biologically active moiety.

35. The method of claim 33;
wherein the biologically active moiety is selected from the group consisting of small molecule biologically active agents and biopolymers.

36. The prodrug of claim 35;
wherein the biologically active moiety is a biopolymer selected from the group consisting of proteins, polypeptides, oligonucleotides and peptide nucleic acids.

37. The method of claim 36;
wherein the biopolymer is a polypeptide selected from the group consisting of ACTH, adenosine deaminase, agalsidase, albumin, apha-1 antitrypsin (AAT), apha-1 proteinase inhibitor (API), alteplase, anistreplase, ancrod serine protease, antibodies (monoclonal and polyclonal, and fragments and fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idurnonidase, immune globulins, influenza vaccines, interleukins (1 alpha, 1 beta, 2, 3, 4, 6, 10, 11, 12), IL-1 receptor antagonist (rhIL-1ra), insulins, interferons (alpha 2a, alpha 2b, alpha 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines, and plant protein.

38. The method of claim 36;
wherein the biopolymer is a protein prepared by recombinant DNA technology.

39. The method of claim 36;
wherein the biopolymer is a protein selected from the group consisting of antibody fragments, single chain binding proteins, catalytic antibodies, and fusion proteins.

40. The method of claim 35;
wherein the biologically active moiety is a small molecule biologically active agent selected from the group consisting of central nervous system-active agents, anti-infective, anti-neoplastic, antibacterial, anti-fungal, analgesic, contraceptive, anti-inflammatory, steroidal, vasodilating, vasoconstricting, and cardiovascular agents with at least one primary or secondary amino group.

41. The method of claim 35;
wherein the biologically active moiety is a small molecule biologically active agent selected from the group consisting of daunorabicin, doxorubicin, idarabicin, mitoxantron, aminoglutethimide, amantadine, diaphenylsulfon, ethambutol, sulfadiazin, sulfamerazin, sulfamethoxazol, sulfelen, clinafloxacin, moxifloxacin, ciptofloxaxin, enoxaci[alpha], norfloxacin, neomycin B, sprectinomycin, kanamycin A, meropenem, dopamin, dobutamin, lisinopril, serotonin, acivicin, and carbutamid.

42. The method of claim 33;
wherein the third step is carried out in an extra-cellular fluid.

43. The method of claim 33;
wherein the substantially non-enzymatic reaction comprises a step of hydrolysis.

44. A method of reacting the polymeric prodrug according to claim 1, comprising:
cleaving the amine-containing moiety from the carrier by a substantially non-enzymatic reaction of the nucleophile-containing linker.

45. The method of claim 44;
wherein the substantially non-enzymatic reaction is carried out at a pH of approximately 7.4.

46. The method of claim 44;
wherein the amine-containing moiety attached to the carrier is cleaved in an extra-cellular fluid.

47. The method of claim 44;
wherein the substantially non-enzymatic reaction comprises a step of hydrolysis.

48. The method of claim 44;
wherein the amine-containing moiety is a biologically active moiety.

49. A method of providing a therapeutically useful concentration of a biologically active molecule comprising:
cleaving, in vivo, the biologically active molecule from the prodrug according to claim 1.

50. The prodrug of claim 11;
wherein R1 is a polyalkyloxy-based polymer selected from the group consisting of polypropylene glycol) and poly (ethylene glycol).

* * * * *